US012693036B2

(12) United States Patent　　　　(10) Patent No.:　US 12,693,036 B2
Pal et al.　　　　　　　　　　　　　　(45) Date of Patent:　　Jul. 28, 2026

(54) SYSTEMS AND PROCESSES FOR DETECTING AEROSOLIZED VIRAL LOADS

(71) Applicant: Opteev Technologies, Inc., Baltimore, MD (US)

(72) Inventors: Biplab Pal, Ellicot City, MD (US); Conrad Bessemer, Millersville, MD (US)

(73) Assignee: Opteev Technologies, Inc., Baltimore, MD (US)

( * ) Notice: Subject to any disclaimer, the term of this patent is extended or adjusted under 35 U.S.C. 154(b) by 601 days.

(21) Appl. No.: 18/150,065

(22) Filed: Jan. 4, 2023

(65) Prior Publication Data

US 2023/0408121 A1　　Dec. 21, 2023

Related U.S. Application Data

(60) Provisional application No. 63/296,446, filed on Jan. 4, 2022.

(51) Int. Cl.
　　*F24F 11/30*　　　　(2018.01)
　　*G01N 33/497*　　　(2006.01)
　　*F24F 110/64*　　　(2018.01)

(52) U.S. Cl.
　　CPC ............ *F24F 11/30* (2018.01); *G01N 33/497* (2013.01); *F24F 2110/64* (2018.01)

(58) Field of Classification Search
　　None
　　See application file for complete search history.

(56) References Cited

U.S. PATENT DOCUMENTS

| | | | |
|---|---|---|---|
| 4,288,544 A | 9/1981 | Suzuki et al. | |
| 8,859,297 B2 | 10/2014 | Alocilja et al. | |
| 8,932,525 B1 * | 1/2015 | Ahmad ................ | G01N 33/497 |
| | | | 422/50 |
| 9,424,734 B1 | 8/2016 | Hagi et al. | |
| 10,327,692 B2 | 6/2019 | Uchiyama | |
| 2003/0186351 A1 | 10/2003 | Machida et al. | |

(Continued)

FOREIGN PATENT DOCUMENTS

| | | |
|---|---|---|
| EP | 2459984 B1 | 6/2018 |
| IN | 2020-21002188 | 7/2021 |

(Continued)

OTHER PUBLICATIONS

ISR and Written Opinion of PCT/US2022/014873 dated May 23, 2022.

(Continued)

*Primary Examiner* — Brian R Gordon
(74) *Attorney, Agent, or Firm* — Fox Rothschild LLP

(57)　　　　　ABSTRACT

Systems are provided for measuring the conductivity of a liquid medium or a gel-like solid or semi-solid medium in which airborne viruses have been forced to fall; and monitoring the resulting changes in the capacitive and resistive properties of the medium due to colloidal electrochemistry of the viral particles using a range of frequency detection techniques. Various control parameters can be implemented to facilitate the estimation of very low viral concentration levels in the medium. The control parameters can include, for example, the level of the medium, the temperature of the medium, statistical classification parameters, and the addition of a buffer to the medium to amplify the signal.

25 Claims, 26 Drawing Sheets

(56) References Cited

U.S. PATENT DOCUMENTS

| | | | |
|---|---|---|---|
| 2004/0239344 A1 | 12/2004 | Hu | |
| 2005/0003396 A1 | 1/2005 | Ozkan et al. | |
| 2007/0167853 A1* | 7/2007 | Melker | A61B 5/411 |
| | | | 600/529 |
| 2011/0252868 A1* | 10/2011 | Doring | G01N 33/497 |
| | | | 73/25.02 |
| 2012/0085927 A1 | 4/2012 | Maeng et al. | |
| 2012/0225423 A1 | 9/2012 | Schwoebel et al. | |
| 2012/0252003 A1 | 10/2012 | Schmera et al. | |
| 2015/0355133 A1 | 12/2015 | Prasad | |
| 2016/0025677 A1 | 1/2016 | Chung et al. | |
| 2017/0227486 A1 | 8/2017 | Bhansali et al. | |
| 2019/0120821 A1* | 4/2019 | Atsalakis | A61B 5/087 |
| 2019/0226704 A1* | 7/2019 | Lundgreen | F24F 11/30 |
| 2019/0232282 A1 | 8/2019 | Pierson et al. | |
| 2019/0250153 A1 | 8/2019 | Muthukumar et al. | |
| 2020/0240939 A1 | 7/2020 | Prasad et al. | |
| 2021/0130197 A1* | 5/2021 | Fraser | F24F 8/192 |
| 2021/0239635 A1 | 8/2021 | Prasad et al. | |
| 2021/0386317 A1 | 12/2021 | Prasad et al. | |
| 2022/0018797 A1 | 1/2022 | Botte et al. | |
| 2022/0192535 A1* | 6/2022 | Atsalakis | A61B 5/097 |
| 2022/0196268 A1* | 6/2022 | Goel | F24F 8/22 |
| 2023/0152199 A1* | 5/2023 | Pal | G01N 27/04 |
| | | | 205/777.5 |
| 2024/0081674 A1* | 3/2024 | Prasad | G01N 33/497 |
| 2024/0255458 A1* | 8/2024 | Markvicka | G01N 33/5438 |

FOREIGN PATENT DOCUMENTS

| | | | |
|---|---|---|---|
| KR | 10-2017-0096092 A | 8/2017 | |
| KR | 10-1934946 B1 | 1/2019 | |
| WO | WO 2005-031300 A2 | 4/2005 | |
| WO | WO 2007-104058 A2 | 9/2007 | |
| WO | WO 2012/047865 A2 | 4/2012 | |
| WO | WO 2019-142599 A1 | 7/2019 | |

OTHER PUBLICATIONS

ISR and Written Opinion of PCT/US2021/061129 dated Mar. 18, 2022.

ISR and Written Opinion of PCT/US2021/048296 dated Dec. 21, 2021.

https://www.epa.gov/air-emissions-monitoring-knowledge-base/monitoring-control-technique-fabric-filters.

https://www.ncbi.nlm.nih.gov/pmc/articles/PMC7094991/.

https://www.epa.gov/pm-pollution/health-and-environmental-effects-particulate-matter-pm.

Alkhouri, et al., "Analysis of breath volatile organic compounds as a noninvasive tool to diagnose nonalcoholic fatty liver disease in children," European journal of gastroenterology & hepatology, vol. 26, No. 1, pp. 82-87, 2014.

Alkhouri, et al.; "Isoprene in the Exhaled Breath is a Novel Biomarker for Advanced Fibrosis in Patients with Chronic Liver Disease: A Pilot Study Clinical and Translational Gastroenterology" 6(9): p. e112, Sep. 2015. | DOI: 10.1038/ctg.2015.40.

* cited by examiner

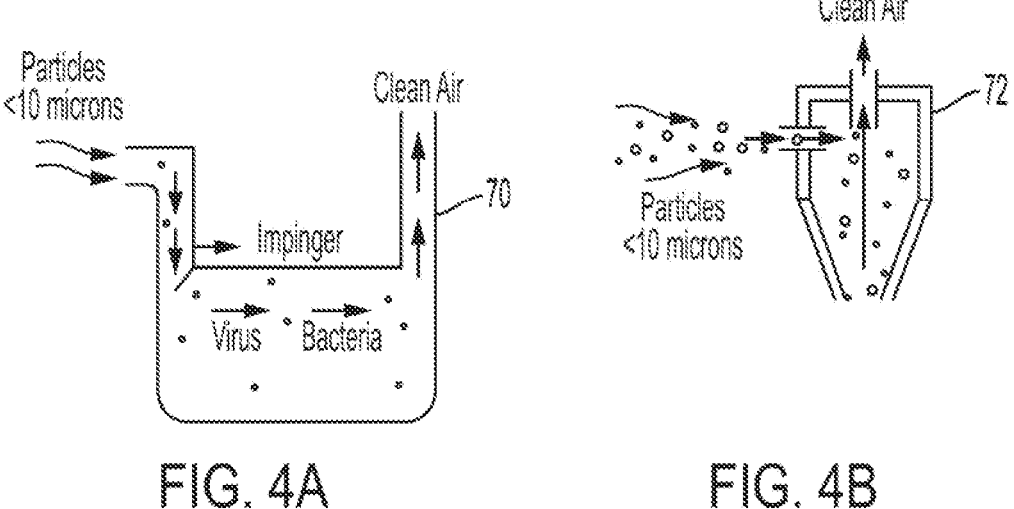
FIG. 4A                          FIG. 4B

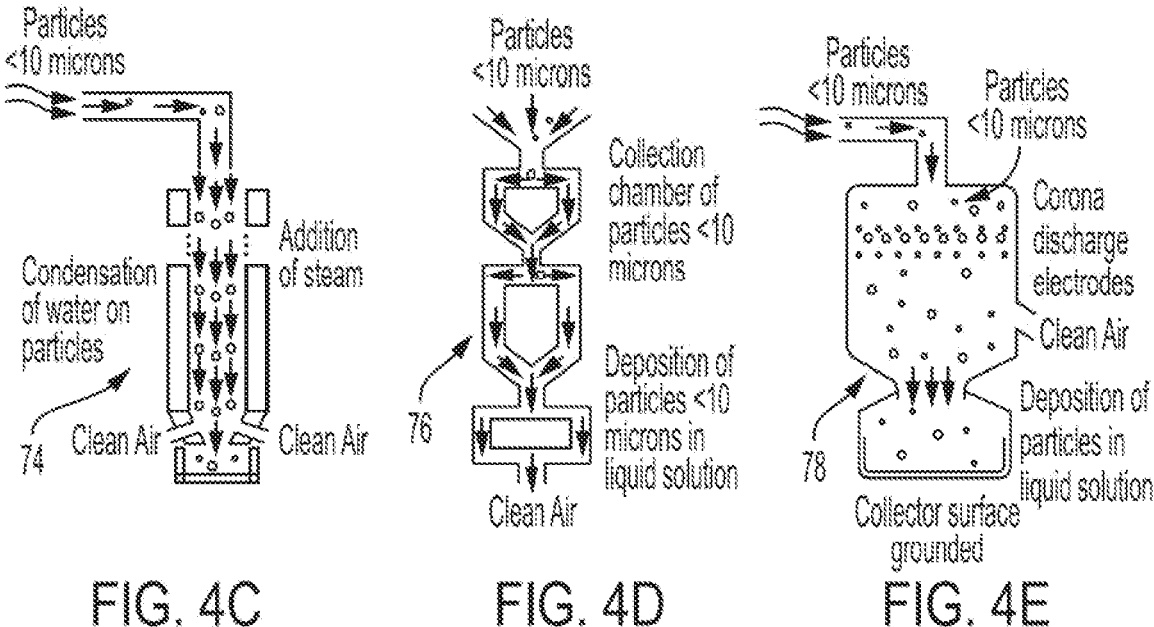

Particles
<10 microns

Condensation
of water on
particles

Addition
of steam

Clean Air          Clean Air

Particles
<10 microns

Collection
chamber of
particles <10
microns

76

Deposition of
particles <10
microns in
liquid solution

Clean Air

FIG. 4D

Particles
<10 microns          Particles
<10 microns

Corona
discharge
electrodes

Clean Air

78          Deposition of
particles in
liquid solution

Collector surface
grounded

FIG. 4E

Obj.; Choice of Medium

PharmaGrade + Tris

| Proportion of Train Test | Model Used | | | | | | | | | | | | | | | | | |
| --- | --- | --- | --- | --- | --- | --- | --- | --- | --- | --- | --- | --- | --- | --- | --- | --- | --- | --- |
| | Logistic Regression | | | Random Forest | | | CART (Decision Tree) | | | KNN | | | Naïve Bayes | | | SVM | | |
| | Acc. | Pre. | Recall | Acc. | Pre. | Recall | Acc. | Pre. | Recall | Acc. | Pre. | Recall | Acc. | Pre. | Recall | Acc. | Pre. | Recall |
| 80/20 | 61.11 | 80.95 | 41.46 | 72.22 | 83.87 | 63.41 | 70.83 | 85.71 | 58.53 | 58.33 | 73.91 | 41.46 | 55.55 | 69.56 | 39.02 | 62.50 | 66.60 | 43.47 |
| 70/30 | 52.08 | 50 | 52.17 | 79.16 | 80.95 | 73.91 | 72.91 | 70.83 | 73.91 | 68.75 | 72.22 | 56.52 | 62.5 | 64.70 | 47.82 | 51.38 | 87.50 | 17.07 |

DDI + Tris

| Proportion of Train Test | Model Used | | | | | | | | | | | | | | | | | |
| --- | --- | --- | --- | --- | --- | --- | --- | --- | --- | --- | --- | --- | --- | --- | --- | --- | --- | --- |
| | Logistic Regression | | | Random Forest | | | CART (Decision Tree) | | | KNN | | | Naïve Bayes | | | SVM | | |
| | Acc. | Pre. | Recall | Acc. | Pre. | Recall | Acc. | Pre. | Recall | Acc. | Pre. | Recall | Acc. | Pre. | Recall | Acc. | Pre. | Recall |
| 80/20 | 51.78 | 53.12 | 58.62 | 48.21 | 50 | 37.93 | 51.78 | 54.16 | 44.82 | 58.92 | 62.5 | 51.72 | 55.35 | 59.09 | 44.82 | 52.08 | 72.72 | 15.68 |
| 70/30 | 51.19 | 52.38 | 51.16 | 55.95 | 57.89 | 51.16 | 51.19 | 52.38 | 51.16 | 55.95 | 57.89 | 51.16 | 48.80 | 50 | 37.20 | 51.19 | 51.92 | 62.79 |

SYSTEMS AND PROCESSES FOR DETECTING AEROSOLIZED VIRAL LOADS

BACKGROUND

COVID-19 and other viruses are spread through airborne transmission. It is known that maintaining good air circulation and low particulate levels within indoor spaces are some of the most effective ways to reduce the risk for humans to become infected by such viruses. Since the beginning of the COVID-19 pandemic, hundreds of products have been released in the market with the goal of achieving greater indoor air circulation and filtering, based on the assumption that these factors will lead to a virus-free airspace. Virus particles ejected from the human body by sneezing and exhaling, however, can have a relatively high velocity that makes it difficult to remove all of the particles from an indoor air space in an efficient and effective manner. Thus, no air circulation system or air filtration system can protect humans from airborne viruses and other pathogens with absolute efficacy and reliability. Also, chemical and ion-based air purification systems can present logistical and safety-related challenges, because these types of systems can be harmful to human health and thus can be used only when humans are not present.

SUMMARY

The disclosed technology relates to systems and processes for detecting airborne viral loads. The technology addresses drawbacks of present air purification systems by accurately determining whether a space contains a detectable level of virus particles, thereby helping to identify the location and origin of an infection or potential infection. The systems and techniques also can be used to determine whether an air purification system is working effectively, by continually checking whether the airborne viral load in a space decreases following the sudden introduction of a virus into the space caused by, for example, the entrance of an infected person. Also, because airborne viruses can be spread via breathing and sneezing, an Internet of Things (IoT) based system such as that disclosed herein can be used readily to inform occupants throughout a building or other living space whether any part of the building or living space is sensing a higher viral load, and thus can act both as a locator of virus-spreading sources, and a warning system. Even if no air filtering or purification system is present in a particular space, which is common in public gatherings, the detection of viral loads by the disclosed system can be highly useful information because it can identify the need to disperse the gathering for safety-related reasons.

In one aspect of the disclosed technology, when a group of aerosolized virus particles are partially or fully dissolved or suspended in a solvent in the form of a liquid medium or a gel like solid/semi-solid medium, the particle count, i.e., the total number of virus particles, referred to hereinafter as the viral load, can be determined by estimating temporal features of the resulting conductivity signal from the medium around a specific frequency range and, optionally, by deploying a homodyne or heterodyne detection technique in which a reference medium free of virus particles is used to provide a reference frequency so that changes in the frequency of the conductivity signal from the medium are amplified and a larger signal to noise ratio thus can be achieved. If a reference medium and homodyne or hetero-dyne detection are not used, however, the viral load never-theless can be determined based on the changes in the frequency of the conductivity signal from the medium, but with a reduced signal to noise ratio.

In another aspect of the disclosed technology, if a certain volume of air is passed over the medium over a period of time and the virus is separated from the air using particle separation techniques, such as electrostatic, gravimetric, or centrifugal separation techniques; and the virus is injected into the medium, the temporal/frequency domain change of conductivity of the medium can provide a good indication of viral load in the air. An electrochemical system employing this technique includes an air suction means; a virus separator; a virus injector; a specially engineered medium to receive effective charge transfer from RNA/DNA viruses; a differential conductivity meter that uses a difference in frequency to detect changes in viral loads; and a computing system, such as an edge computer, to estimate the viral load of the air from estimated temporal and, optionally, differ-ential changes in the conductivity of the medium. Once the change is detected and a substantial viral load is confirmed or validated by an algorithm, the system can send an alarm signal and/or an activation signal via wireless or wireline transmission to an air disinfection system, a cleaning system, and/or concerned users.

In another aspect of the disclosed technology, a system is provided for measuring the conductivity of a liquid medium or a gel-like solid or semi-solid medium in which airborne viruses have been forced to fall; and the resulting changes in the capacitive and resistive properties of the medium due to colloidal electrochemistry of the viral particles are moni-tored using a range of frequency detection techniques including, optionally, differential frequency detection tech-niques. Various control parameters can be implemented to facilitate the estimation of very low viral concentration levels in the medium. The control parameters can include, for example, the level of the medium, the temperature of the medium, statistical classification parameters, and the addi-tion of a buffer to the medium to amplify the signal.

In another aspect of the disclosed technology, a method is provided for mechanically injecting a virus into a liquid or gel like solid/semi-solid medium that includes a dopant solution which neutralizes the virus faster and thus can facilitate the creation of a stronger and faster detection signal than would be possible otherwise.

In another aspect of the disclosed technology, a system for detecting the presence of a viral load in an airspace includes a conductivity probe; and a frequency generator communi-catively coupled to the conductivity probe and configured to, during operation, apply an alternating voltage to the con-ductivity probe while the conductivity probe is immersed at least in part in a medium that includes a solvent, and particles sampled from the airspace and suspended in the solvent. The first alternating voltage causes an alternating current to flow between the conductivity probe and the frequency generator. The system further includes a comput-ing device communicatively coupled to the frequency gen-erator and configured to, during operation, determine a viral load in the medium based on a frequency response of the conductivity probe to the alternating voltage applied thereto.

In another aspect of the disclosed technology, system is further configured to, during operation, determine the viral load in the medium based on a correlation between the frequency response of the conductivity probe to the alter-nating voltage applied thereto, and the viral load.

In another aspect of the disclosed technology, the system further incudes the medium, wherein the solvent is one of a liquid and a gel-like solid or semi-solid.

In another aspect of the disclosed technology, the solvent is selected from a class of materials capable of acting as a base of a colloidal suspension in which the particles are suspended after being separated from the airspace, and further capable of effecting a transfer of charge between particles and the solvent.

In another aspect of the disclosed technology, the solvent is one of deionized water; distilled water; isopropyl alcohol; ultra-low molal tris-salt medium; a mild basic salt medium; and disodium laureth sulfosuccinate medium.

In another aspect of the disclosed technology, the solvent has conductivity of about one microsiemens or less.

In another aspect of the disclosed technology, the computing device is further configured to, during operation, extract one or more signal artifacts from a signal representing the frequency response of the conductivity probe to the alternating voltage applied thereto; and to correlate the viral load in the medium with the one or more signal artifacts to thereby reduce or eliminate false positives and false negatives in the viral load determined by the computing device.

In another aspect of the disclosed technology, the signal representing the frequency response of the conductivity probe to the alternating voltage applied thereto is a temporal signal.

In another aspect of the disclosed technology, the signal representing the frequency response of the conductivity probe to the alternating voltage applied thereto is a frequency-based signal representing the conductivity of the medium.

In another aspect of the disclosed technology, the computing device is further configured to correlate the one or more signal artifacts with the viral load in the medium using a rule engine developed from a machine learning technique.

In another aspect of the disclosed technology, the computing device is further configured to reduce or eliminate false positives and false negatives in the viral load determined by the computing device using at least one of a particulate matter level, a carbon dioxide level, and the presence or absence of people in the airspace.

In another aspect of the disclosed technology, the conductivity probe is a first conductivity probe; the frequency generator is a first frequency generator; and the medium is a first medium. The system further includes a second conductivity probe; and a second frequency generator communicatively coupled to the second conductivity probe and configured to, during operation, apply a second alternating voltage to the second conductivity probe while the second conductivity probe is immersed at least in part in a second medium that includes the solvent. The second alternating voltage causes a second alternating current to flow between the second conductivity probe and the second frequency generator. The system further incudes a differential frequency detector communicatively coupled to the first and second frequency generators and the computing device and configured to, during operation, determine a frequency differential between the frequencies of the first and second alternating currents. The computing device is further configured to, during operation, determine the viral load in the first medium based on the frequency differential.

In another aspect of the disclosed technology, the second medium is free of virus particles.

In another aspect of the disclosed technology, the computing device is further configured to determine a pattern difference between signals representing the frequency responses of the first and second conductivity probes to the respective first and second alternating voltages applied thereto, wherein the patterns are artifacts of the signals.

In another aspect of the disclosed technology, the computing device is further configured to, during operation, determine the viral load in the first medium using one of a homodyne and a heterodyne detection technique.

In another aspect of the disclosed technology, the computing device is further configured to estimate the viral load in the airspace based on the viral load in the first medium.

In another aspect of the disclosed technology, the computing device is further configured to generate and send a notification when the viral load in the airspace is determined to be greater than a predetermined value.

In another aspect of the disclosed technology, the system further includes a visual altering device communicatively coupled to the computing device. The computing device is further configured to generate an output when the viral load in the airspace is determined to be greater than a predetermined value; and the visual alerting device is configured to generate a visual alert in response to the output of the computing device.

In another aspect of the disclosed technology, the system further includes an audible altering device communicatively coupled to the computing device. The computing device is further configured to generate an output when the viral load in the airspace is determined to be greater than a predetermined value; and the audible alerting device is configured to generate an audible alert in response to the output of the computing device.

In another aspect of the disclosed technology, the computing device is an edge-cloud server.

In another aspect of the disclosed technology, the system further includes a particle collector in fluid communication with the airspace and configured to, during operation, separate the particles from a sample of the airspace.

In another aspect of the disclosed technology, the particle collector includes a coarse filter configured to remove from the sample of the airspace particles having a size greater than a predetermined value.

In another aspect of the disclosed technology, the coarse filter is configured to remove from the sample of the airspace particles having an aerodynamic diameter greater than about ten microns.

In another aspect of the disclosed technology, the particle collector further includes a particle separator configured to remove from the sample of the airspace the particles sampled from the airspace.

In another aspect of the disclosed technology, the system further includes a fan in fluid communication with the particle collector and configured to, during operation, direct the sample from the airspace and to the particle collector.

In another aspect of the disclosed technology, the system further includes a tube, such as the type of tube used on breathalyzer machines, in fluid communication with an interior of a chamber holding the solvent. The tube is configured so that a person can breathe into the tube and thereby introduce the virus into the solvent via the tube, so that the system can provide an indication as to whether the person is infected with a virus such as COVID-19.

In another aspect of the disclosed technology, a process for detecting the presence of a viral load in an airspace includes providing a solvent; obtaining an air sample from the airspace;

and separating particles from the air sample so that the particles become suspended in the solvent to form a medium. The process also includes immersing at least a portion of a conductivity probe in the medium; applying an alternating voltage to the conductivity probe; and determining a viral load in the medium based on a frequency response of the conductivity probe to the alternating voltage applied thereto.

In another aspect of the disclosed technology, determining a viral load in the medium based on a frequency response of the conductivity probe to the alternating voltage applied thereto includes determining the viral load in the medium based on a correlation between the frequency response of the conductivity probe to the alternating voltage applied thereto, and the viral load.

In another aspect of the disclosed technology, providing a solvent includes selecting the solvent from a class of materials capable of acting as a base of a colloidal suspension in which the particles are suspended after being separated from the airspace, and further capable of effecting a transfer of charge between the particles and the solvent.

In another aspect of the disclosed technology, the process further includes reducing or eliminating false positives and false negatives in the viral load determination by extracting one or more signal artifacts from a signal representing the frequency response of the conductivity probe to the alternating voltage applied thereto; and correlating the viral load in the medium with the one or more signal artifacts.

In another aspect of the disclosed technology, correlating the viral load in the medium with the one or more signal artifacts includes correlating the viral load in the medium with the one or more signal artifacts using a rule engine developed from a machine learning technique.

In another aspect of the disclosed technology, the process further includes reducing or eliminating false positives and false negatives in the viral load determination using at least one of a particulate matter level, a carbon dioxide level, and the presence or absence of people in the airspace.

In another aspect of the disclosed technology, the conductivity probe is a first conductivity probe; the medium is a first medium; and the alternating voltage is a first alternating voltage. The process further includes providing a second conductivity probe; and applying a second alternating voltage to the second conductivity probe while the second conductivity probe is immersed at least in part in a second medium that includes the solvent. The process also includes determining a differential between the frequency response of the first conductivity probe to the alternating voltage applied thereto and a frequency response of the second conductivity probe to the alternating voltage applied thereto; and determining the viral load in the medium based on the frequency differential.

In another aspect of the disclosed technology, the second medium is free of virus particles.

In another aspect of the disclosed technology, determining the viral load in the medium based on the frequency differential includes determining the viral load in the first medium based on one of a homodyne and a heterodyne frequency detection technique.

In another aspect of the disclosed technology, determining a viral load in the medium based on the frequency differential includes determining the viral load in the medium based on a predetermined relationship between the viral load in the first volume and the frequency differential.

In another aspect of the disclosed technology, the process further includes maintaining the first and second media at substantially the same temperature.

In another aspect of the disclosed technology, the process further includes estimating the viral load in the airspace based on the viral load in the medium.

In another aspect of the disclosed technology, the process further includes generating and sending a notification when the viral load in the airspace is determined to be greater than a predetermined value.

In another aspect of the disclosed technology, separating particles from the air sample so that the particles become suspended in the solvent to form a medium includes separating particles having an aerodynamic diameter of about ten microns or less from the air sample.

In another aspect of the disclosed technology, determining a viral load in the first volume based on a frequency response of the conductivity probe to the alternating voltage applied thereto includes determining a viral load in the first volume based on the frequency response of the conductivity probe to the alternating voltage applied thereto using an edge-cloud server.

In another aspect of the disclosed technology, the process further includes measuring a temperature and a relative humidity of the airspace; and determining a particle concentration in the airspace. The process also includes calculating a minimum separation distance needed to reduce a potential for human-to-human transmission of airborne pathogens, based on an estimate of distance the particles will travel upon being exhaled as determined using the temperature and relative humidity of the airspace, and the particle concentration in the airspace.

In another aspect of the disclosed technology, a combination of virus-air separation system directing virus to a liquid chamber, a frequency-based conductivity signal is fed into a signal processing system which correlates viral load with artifacts of the signal (such as variance, crest factor, higher order moments) and false positive or false negative elimination by signal analysis and combination of other sensor signals.

In another aspect of the disclosed technology, a combination of virus-air separation system directing virus to two liquid chambers (one reference and one probe), a differential frequency-based conductivity measuring in which differential frequency response from both the liquid chamber is fed into a signal processing system and a signal processing system to correlate signal artifacts such as skewness, variance with viral load and elimination of false positive or false negative by signal analysis and combination of other sensor signals In another aspect of the disclosed technology, a class of liquids (such as deionized water, ultra-low molal Tris-salt solution or mild basic salt solutions) that can act as a base of a colloidal solution in which virus is absorbed and this class of liquid can act as quick and effective charge transfer of virus into the liquid media.

In another aspect of the disclosed technology, a system of signal processing unit in which a temporal signal is converted into a number of artifacts such as variance, co-efficient of variation, skewness and many others similar features which has been shown to be correlated with the viral load.

In another aspect of the disclosed technology, a single artifact of the conductivity signal such as variance or a combination of multiple artifacts like variance, skewness etc., used in a rule engine developed from various machine learning techniques such as neural network, SVM, etc., that have been shown or known to correlate with viral load.

In another aspect of the disclosed technology, the elimination of the false positive and false negative reading by combining the viral load data with signals from particulates monitoring (PM sensors 1, 2.5 and 10 micron), proximity detection and carbon dioxide and use the data by a rule engine obtained from various Machine Learning techniques such as SVM (support vector machine), Neural Network, etc.

DESCRIPTION OF THE DRAWINGS

The following drawings are illustrative of particular embodiments of the present disclosure and do not limit the scope of the present disclosure. The drawings are not to scale and are intended for use in conjunction with the explanations provided herein. Embodiments of the present disclosure will hereinafter be described in conjunction with the appended drawings.

FIG. 4A is a diagrammatic illustration of an aerosol sampler the particle collector of the system shown in FIGS. 1-1B, 3A, and 3B.

FIG. 4B is a diagrammatic illustration of an alternative embodiment of the aerosol sampler shown in FIG. 4A.

FIG. 4C is a diagrammatic illustration of another alternative embodiment of the aerosol sampler shown in FIG. 4A.

FIG. 4D is a diagrammatic illustration of another alternative embodiment of the aerosol sampler shown in FIG. 4A.

FIG. 4E is a diagrammatic illustration of another alternative embodiment of the aerosol sampler shown in FIG. 4A.

FIG. 10 is a tabular presentation of the results of a validation process performed using the algorithm shown in FIG. 8.

DETAILED DESCRIPTION

Figure 1:
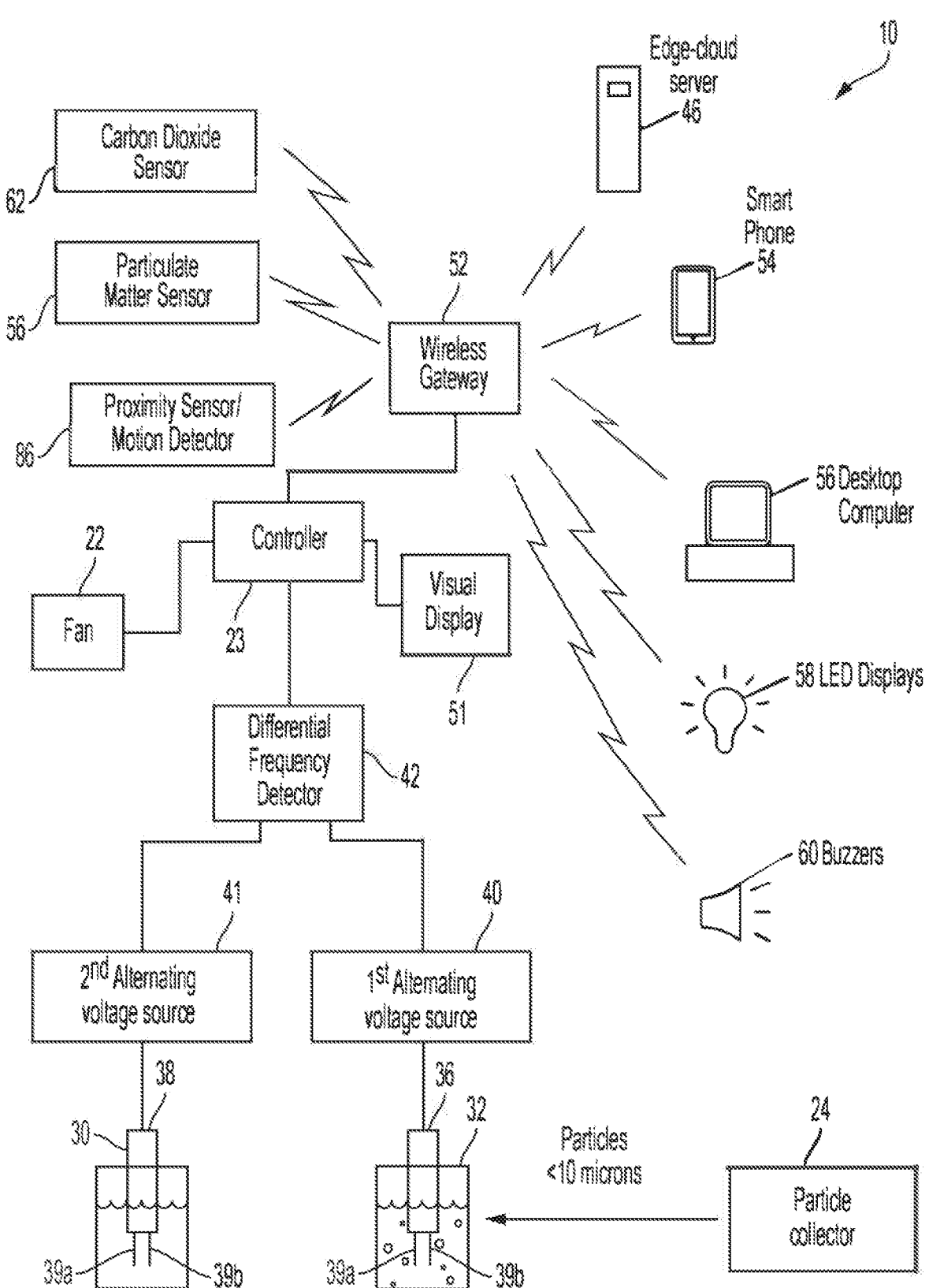
FIG. 1 is a block diagram of a system for detecting aerosolized viral loads.

The inventive concepts are described with reference to the attached figures, wherein like reference numerals represent like parts and assemblies throughout the several views. The figures are not drawn to scale and are provided merely to illustrate the instant inventive concepts. The figures do not limit the scope of the present disclosure or the appended claims. Several aspects of the inventive concepts are described below with reference to example applications for illustration. It should be understood that numerous specific details, relationships, and methods are set forth to provide a full understanding of the inventive concepts. One having ordinary skill in the relevant art, however, will readily recognize that the inventive concepts can be practiced without one or more of the specific details or with other methods. In other instances, well-known structures or operation are not shown in detail to avoid obscuring the inventive concepts.

FIGS. 1-1B, 3A-5, and 11 disclose a system 10 for detecting an airborne viral load, and various components thereof. The system 10 uses alternating current (AC) conductivity measurement to determine the viral load in a colloidal suspension, or "sample medium," formed from airborne virus particles from the monitored space, and a solvent into which the particles have been introduced after being separated from the air. The system 10 also uses a reference medium containing the same solvent, in the same volume, as the solvent used in the sample medium. The reference medium, however, does not include any virus particles. The refence medium is maintained at substantially the same environmental conditions as the sample medium.

An alternating voltage is applied across the electrodes of a first probe immersed in the sample medium, i.e., the colloidal suspension formed by the sampled virus particles and the solvent into which the virus particles have been dispersed. A substantially identical alternating voltage is applied across the electrodes of a second probe immersed in the reference medium. The voltage potential across the electrodes of the first and second probes causes an alternating current to flow through each probe. The difference between the frequencies of the respective alternating currents is determined using a homodyne detection technique. In alternative embodiments, the difference between the frequencies of the respective alternating currents is determined using a heterodyne detection technique.

The differential frequency response of the first and second probes can be used to estimate the viral concentration, including very low viral concentrations, in the sample medium. More specifically, the presence of a viral load in the sample medium affects the electrochemical characteristics of the solvent used to form the sample medium, which in turn affects the electrical conductivity and dielectric properties of the solvent. The change in electrical conductivity and dielectric properties affect the frequency of the alternating current passing between the electrodes of the probe immersed the sample medium by a very small, but detectable, amount. The differential frequency response of the probes immersed in the sample and reference media thus can be correlated to the presence and magnitude of the viral load in the sample medium.

Alternative embodiments of the system 10 can be configured without the reference medium and without the second probe, and without the use of the homodyne or heterodyne detection to determine the differential frequency response of the first and second probes.

Also disclosed are mechanical methods for introducing the virus particles into the solvent; and a dopant that, when added to the solvent, enhances the Zeta potential and Debye radius of the resulting colloidal suspension in which charged virus particles have been trapped, thereby enhancing the overall sensitivity of the detection of the viral load. With the disclosed combination of mechanical, electrical, signal processing, and algorithmic features, the system 10 has been shown to be sensitive enough to detect small viral loads in the range of 100-150 particle/100 mL of air, with a high degree of reliability and repeatability.

The system 10 can be characterized as including, without limitation, three core component groups: an aerosol classification and bio-sampling group; a viral detection group that detects the presence and magnitude of a viral load based on changes in electrical properties of the medium in which viral particles are suspended; and an edge computation and IoT platform group that facilitates the elimination of errors in the acquired data, and generation of notifications and warnings when an airborne virus is detected.

In aerosol sampling, air quality generally is determined by: (i) determining the density of airborne particles of different sizes; (ii) determining the "health" of breathing space, i.e., whether the breathing space is too densely populated, and (iii) determining the air properties to scientifically calculate the air transport characteristics.

Figure 2A:
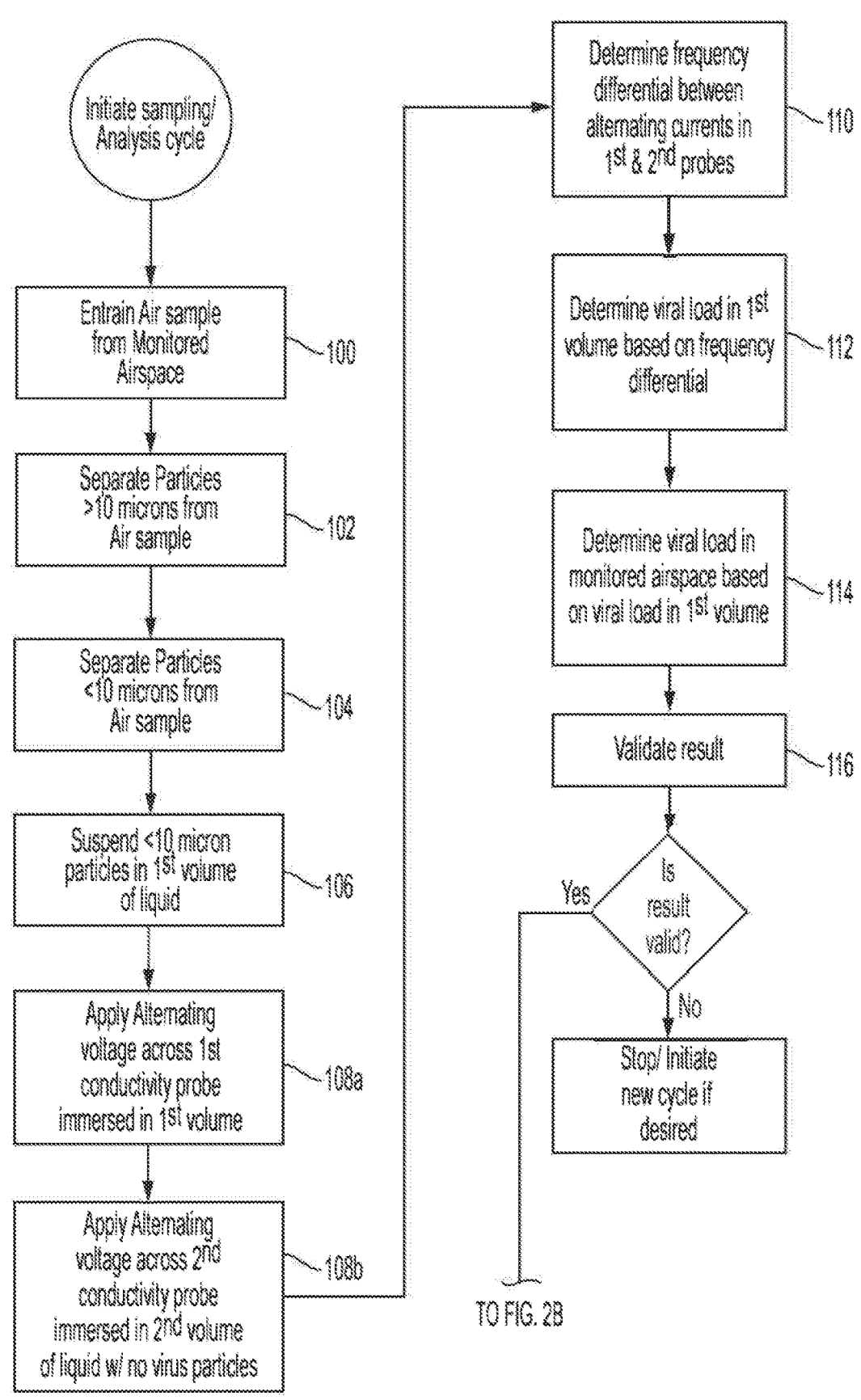
FIGS. 2A-2C are another flow chart depicting operation of the system shown in FIGS. 1-1B.
Figure 2B:
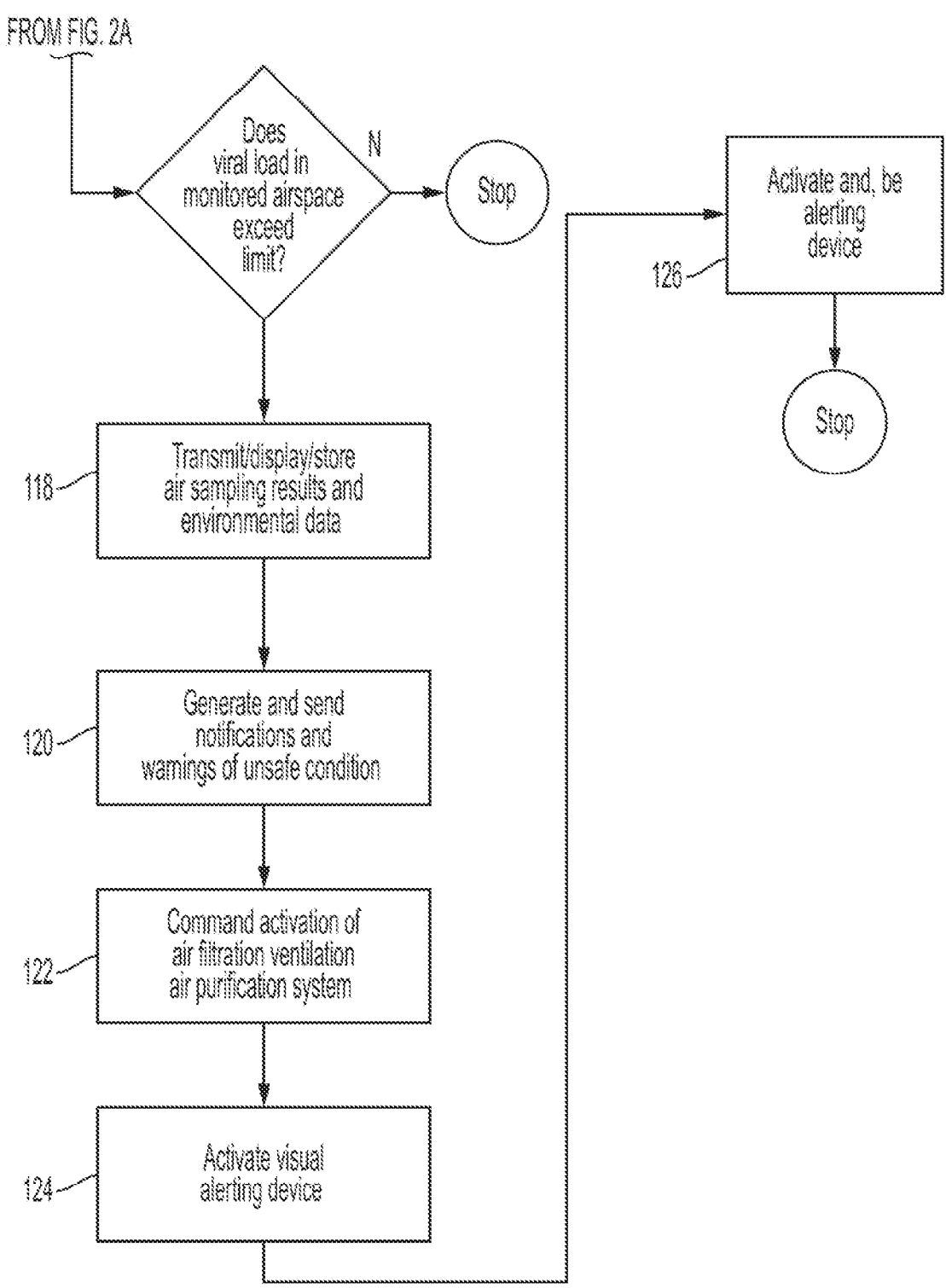
Figure 2C:
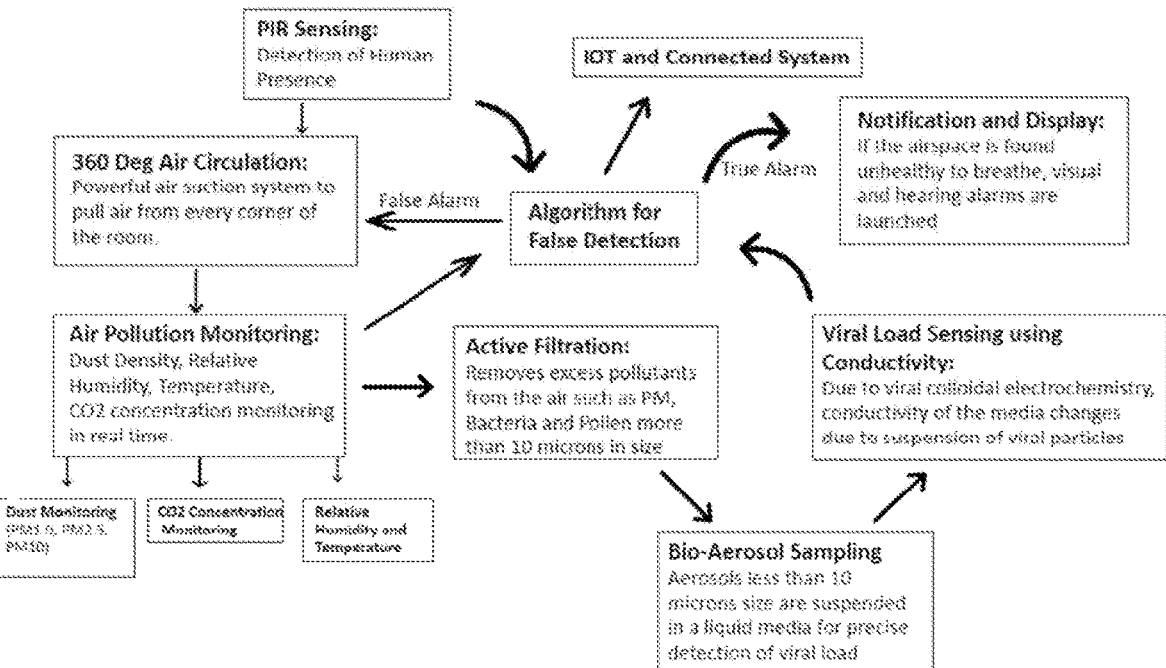

FIGS. 2A-2C are flow charts depicting operation of the system 10. The initial portion of the virus detection process performed by the system 10 comprises collecting air from throughout the room or other space in which the air quality is to be monitored; and isolating particles that potentially are the most conducive to causing an infection and spreading the virus.

Figure 12:
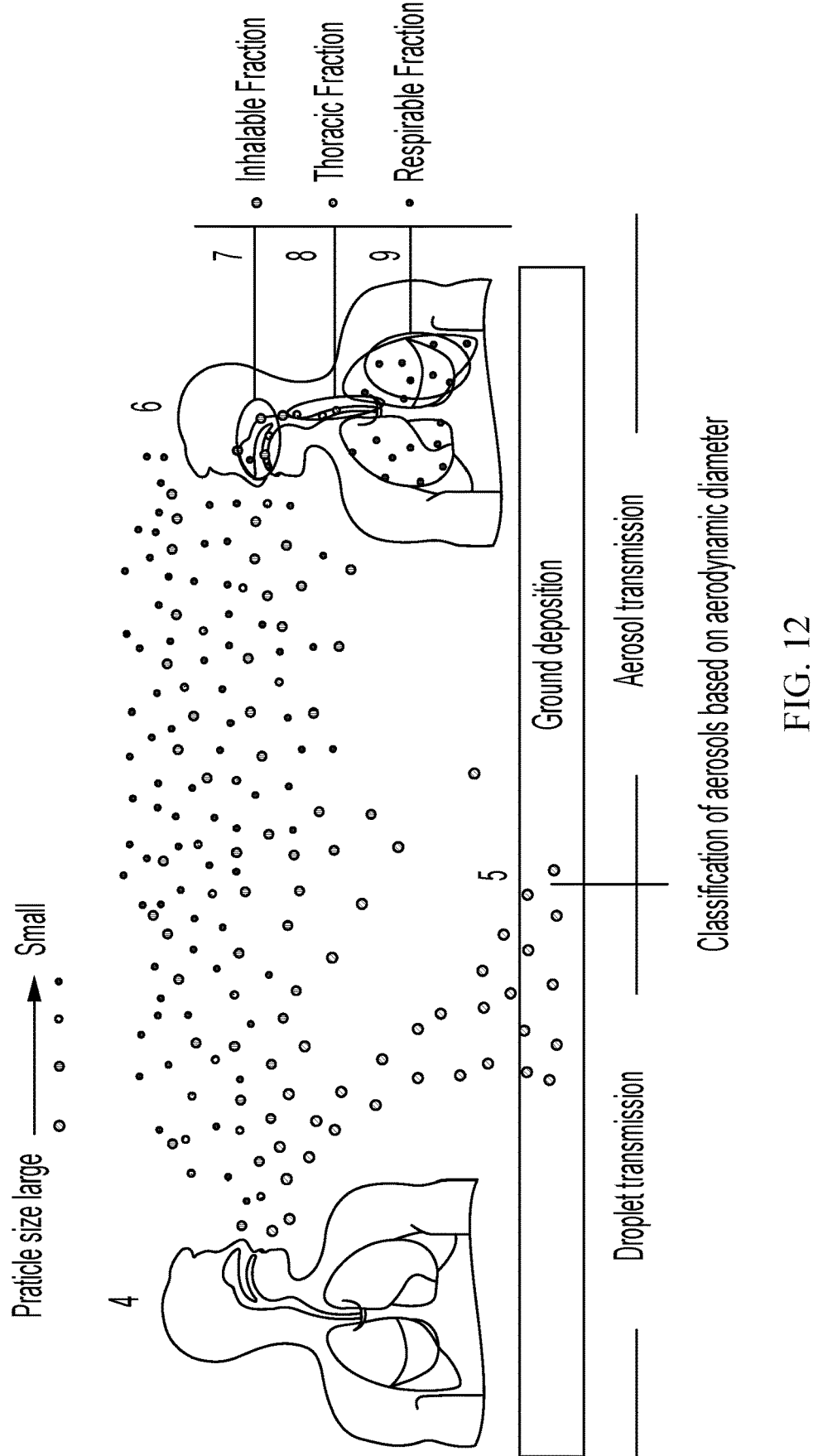
FIG. 12 is a diagrammatic representation depicting the classification of aerosol particles based on their diameters.

Referring to FIG. 12, a person infected with a respiratory virus typically emits a variety of aerosols that can be classified in accordance with their aerodynamic diameter. The aerodynamic diameter of a particle is defined as the diameter of a sphere of density 1 g/cm 3 which suspends or settles in still air at same velocity as the particle. An infected person, in general, can emit aerosolized particles having aerodynamic diameters in the range of about 1 micron to about 200 microns. The particles having an aerodynamic diameter greater than about 100 microns are much less likely to remain airborne than the smaller diameter particles, and settle to the nearby ground very quickly after being emitted. Such particles, therefore, are highly unlikely spread the virus.

Aerosolized particles having an aerodynamic diameter in the range of about ten microns to about 100 microns are characterized as inhalable fractions. Such particles typically become trapped in the nose and mouth, and therefore are unlikely to cause an infection by way of the respiratory system.

Aerosolized particles with an aerodynamic diameter in the range of about four microns to about ten microns are characterized as thoracic fractions. As shown in FIG. 12, these types of particles readily can reach the throat and upper respiratory duct, and therefore are likely to result in infection and spreading of the virus.

Aerosolized particles having an aerodynamic diameter less than about four microns are characterized as respirable fractions. As shown in FIG. 12, these types of particles generally are considered the most dangerous because such particles can reach the finest parts of the lungs. Respirable particles, therefore, are responsible to a large extent for the spread of illnesses caused by airborne viral pathogens.

Thoracic and respirable particles are believed to make up a major portion of the viral load in a typical space in which the COVID-19 virus is spread. And as noted above, these types of particles, if inhaled, are highly likely to cause an infection. Hence, the system 10 is configured to target thoracic and respirable particles when estimating the viral load, to help maximize the detection of such potentially infectious particles, and decrease false readings based on the detection of larger particles.

The system 10 comprises a fan 22, depicted schematically in FIG. 1. The fan 22 is configured to draw ambient air from the space or volume of air being monitored for a viral load (step 100 in FIG. 2A). In one possible embodiment, the fan 22 can be configured to generate a suction that draws air from every direction around the fan 22, and from a distance of up to 12 feet away from the fan 22, to help maximize the area of coverage and the operational efficiency of the system 10. The fan 22 is communicatively coupled to a controller 23 of the system 10, as shown in FIG. 1. The controller 23 is configured activate and deactivate the fan 22 at the start and end of each sampling period.

Figure 1A:
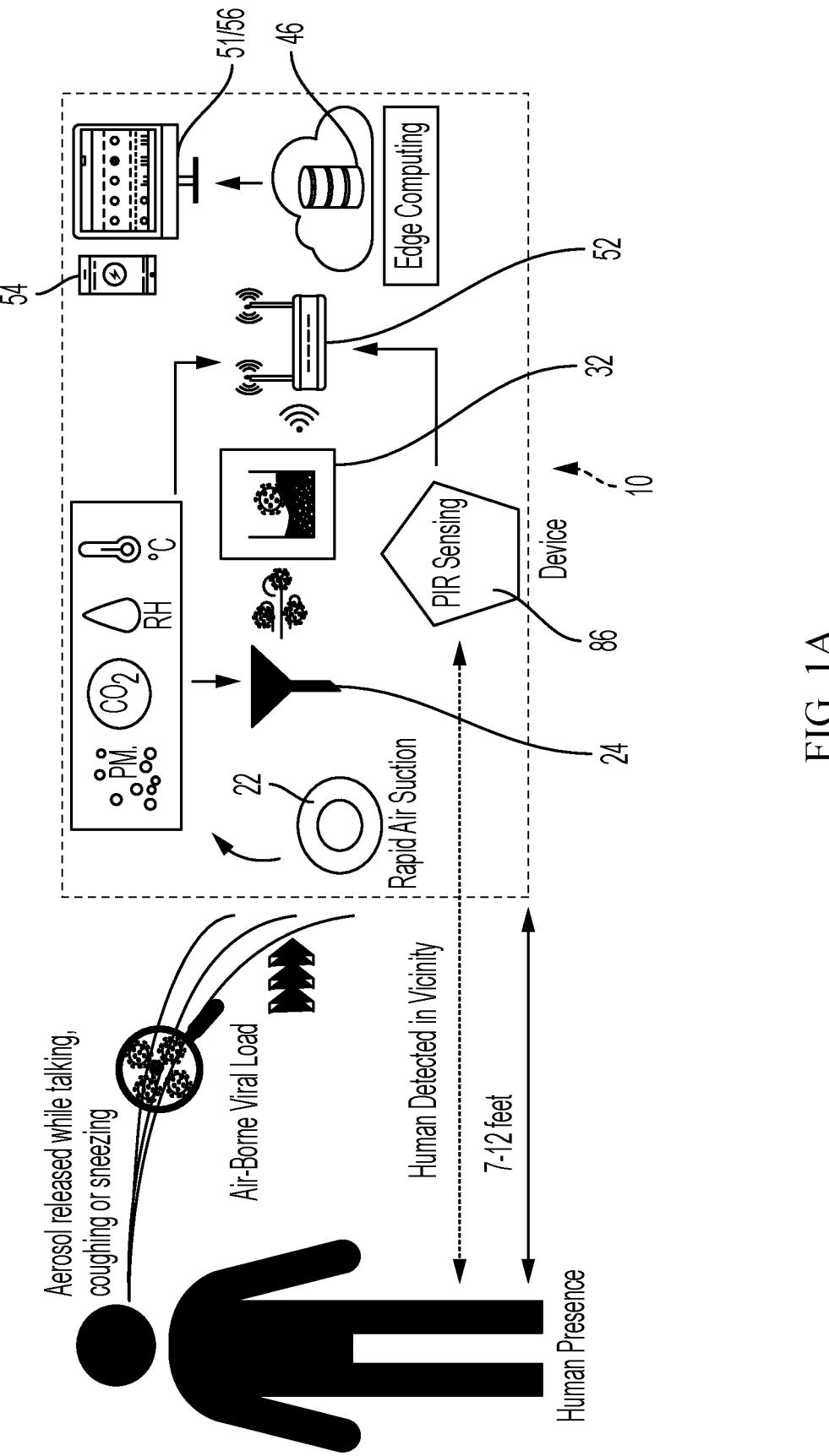
FIG. 1A is diagrammatic illustration of the system shown in FIG. 1.
Figure 1B:
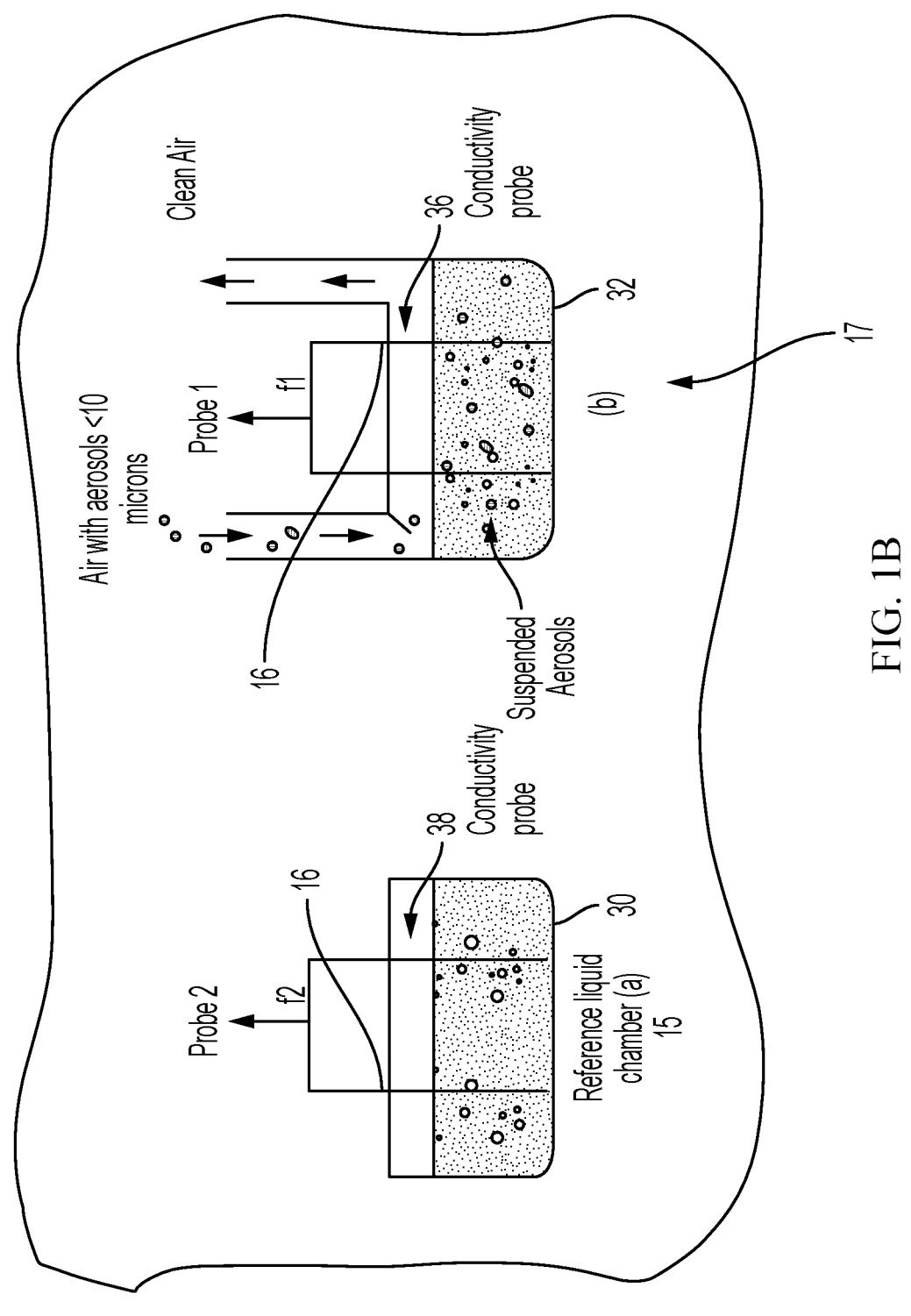
FIG. 1B is a diagrammatic illustration of a sample chamber, a reference chamber, and probes of the system shown in FIGS. 1 and 1A.
Figure 11:
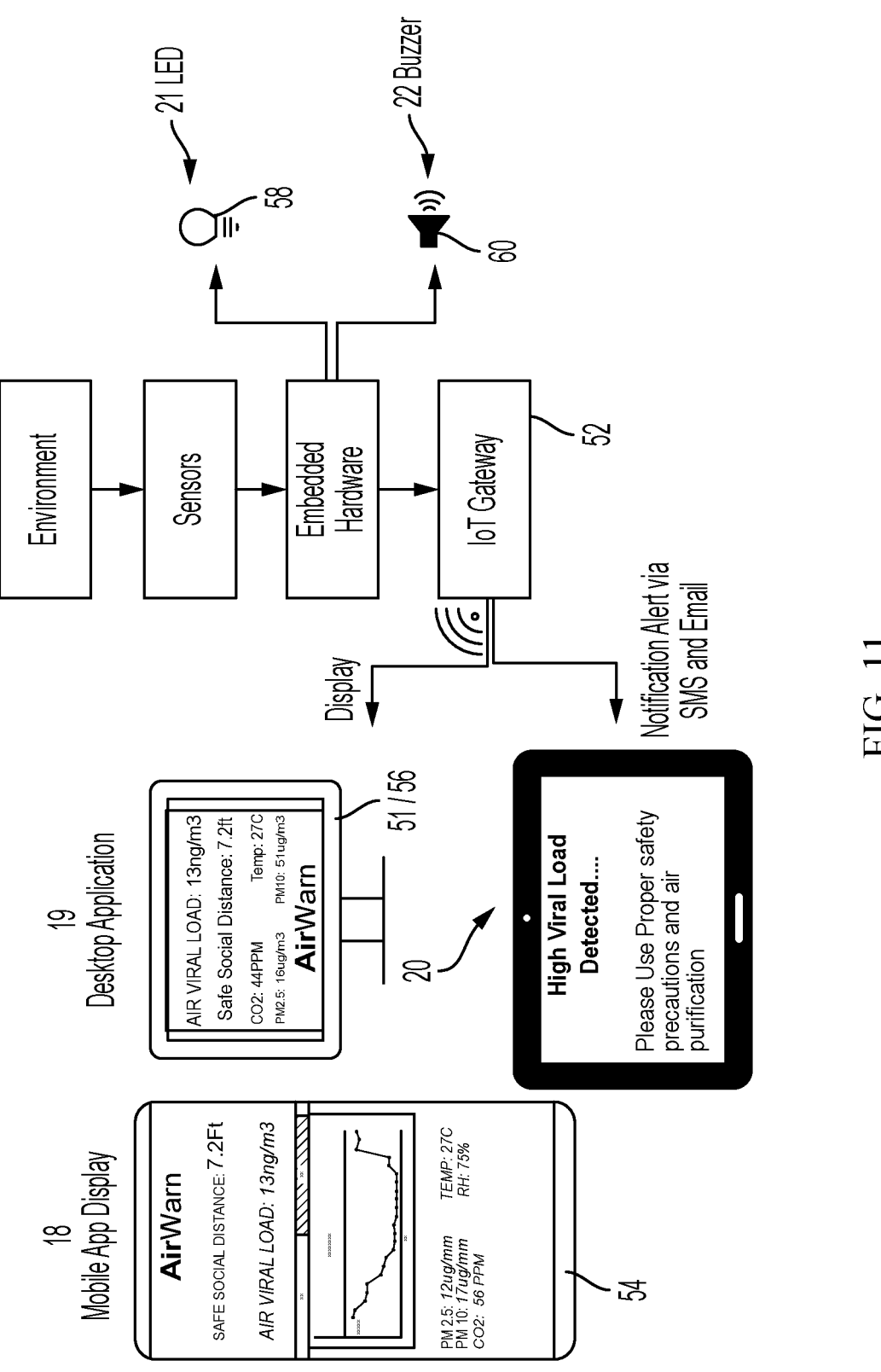
FIG. 11 is a diagrammatic illustration of various display and alert devices of the system shown in in FIGS. 1-1B and 3A-5.

Each sampling period can have a duration of, for example, about ten to about 100 seconds. The controller 23 can be configured to obtain a sample at predetermined intervals, such as about every one minute to about every ten minutes. The system 10 can be configured so that the sampling period and sampling intervals can be varied by the user via inputs provided through a suitable input device communicatively coupled to the controller 23. The system 10 also can be configured so that the user can initiate a sampling period on demand, by entering a command though the input device. The input device can be, for example, a smart phone 54; a desktop computer 56; a server, such as edge-cloud server 46; etc., equipped with a suitable application. The smart phone 54, a desktop computer 56, edge-cloud server 46, and other input devices can be communicatively coupled to the controller 23 by way of a wireless gateway 52 or other suitable means. The smart phone 54, desktop computer 56, edge-cloud server 46, and wireless gateway 52 are shown in FIGS. 1, 1A, and 11.

The controller 23 can be any type of computing device capable of performing the logical operations described therein. As a non-limiting example, the controller 23 can be a microcontroller comprising, in relevant part, a micropro-cessor; a memory communicatively coupled to the micro-processor; and computer executable instructions stored in the memory. The computer executable instructions are con-figured so that, upon execution by the microprocessor, the computer executable instructions cause the microcontroller to perform the logical operations disclosed herein.

The system 10 further comprises a particle collector 24, depicted schematically in FIG. 1. The particle collector 24 is in fluid communication with the fan 22; and is located downstream from the fan 22 so that the particle collector 24 receives the ambient air entrained by the fan 22. The particle collector 24 is configured to collect aerosolized virus par-ticles likely to result in an infection, and to separate and eliminate aerosolized particles of no interest, i.e., larger particles that are unlikely to result in infection.

Figures 3A, 3B:
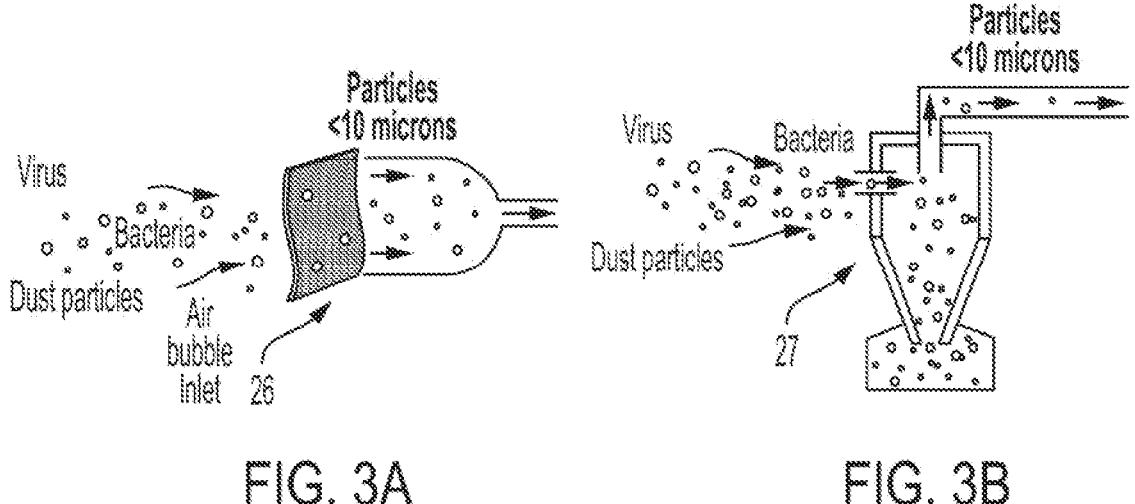
FIG. 3A is a diagrammatic illustration of a coarse filter of a particle collector of the system shown in FIGS. 1-1B
FIG. 3B is a diagrammatic illustration of an alternative embodiment of the coarse filter shown in FIG. 3A.

Referring to FIGS. 3A and 3B, the particle collector 24 comprises a coarse filter that filters out, or eliminates par-ticles having an aerodynamic diameter greater than about ten microns (step 102 in FIG. 2A). As discussed above, virus particles characterized as inhalable fractions, i.e., particles with an aerodynamic diameter greater than about ten microns, are highly unlikely to produce an infection. Thus, these particles are eliminated in the initial, or coarse filtra-tion portion of the aerosol sampling process. The coarse filter can use any suitable technique to eliminate the inhal-able fractions. For example, the coarse filter can comprise a filter mesh 26, shown in FIG. 3A, that captures particles larger than about ten microns. Alternatively, the coarse filter can comprise a cyclonic filter 27, shown in FIG. 3B, having a cut-off particle diameter of about ten microns.

Referring to FIGS. 4A-4E, the particle collector 24 further comprises an aerosol sampler. The sampled air is directed to the aerosol sampler following removal of the inhalable fractions in the coarse filter. The aerosol sampler is config-ured to separate the thoracic and respirable fractions from the air flow after the larger particles have been removed by the coarse air filter (step 102 in FIG. 2A). The aerosol sampler can use any suitable technique to perform this function. For example, as shown diagrammatically in FIG. 4A, the aerosol sampler can comprise an impinger 70 configured to capture aerosolized particles having an aero-dynamic diameter of less than about ten microns.

Alternatively, as shown diagrammatically in FIG. 4B, the aerosol sampler can comprise a cyclonic filter 72 configured to capture aerosolized particles having an aerodynamic diameter of less than about ten microns.

Alternatively, as shown diagrammatically in FIG. 4C, the aerosol sampler can comprise a condensation-based separa-tor 74 configured to introduce steam into the sampled airflow. The resulting condensation of causes aerosolized particles having an aerodynamic diameter of less than about ten microns to drop out of the airflow.

Alternatively, as shown in diagrammatically FIG. 4D, the aerosol sampler can comprise an impactor 76 configured to capture aerosolized particles having an aerodynamic diam-eter of less than about ten microns.

Alternatively, as shown diagrammatically in FIG. 4E, the aerosol sampler can comprise an electrostatic precipitator 78 configured to capture aerosolized particles having an aero-dynamic diameter of less than about ten microns.

The aerosol sampler is configured so that the thoracic and respirable fractions, upon being separated from the air stream, drop into, and become suspended in a dispersion medium, or solvent, positioned beneath the aerosol sampler as shown in FIGS. 4A-4E (step 106 in FIG. 2A). The sampled air from which the thoracic and respirable fractions have been separated is released back in the ambient envi-ronment to complete the bio sampling process.

The solvent into which the separated thoracic and respi-rable fractions are dispersed can be a class of liquids or gel-like solid or semi-solid media such as, for example, deionized water; distilled water; ultra-low molal tris-salt solution, mild basic salt solutions, isopropyl alcohol, diso-dium laureth sulfosuccinate (DLS) solution, and other types of liquids that can act as a base of a colloidal suspension into which virus particles are absorbed and suspended; that become polarized upon the absorption of the virus particles; and that can effect a quick and effective charge transfer between the virus particles and the medium.

After the aerosols are sampled and the thoracic and respirable fractions are suspended in the solvent to form the colloidal suspension, i.e., the sample medium, the system 10 detects whether the suspended particles contain any viruses. Airborne virus particles that have been separated from the air and suspended in a solvent, i.e., a dispersion medium, can change the electrochemical properties of the solvent; and the airborne viral load can be predicted or estimated by mea-suring the change in the electrical properties of the solvent caused by the presence of the virus particles. This in turn can facilitate the determination an airborne viral load in the space from which the particles were obtained.

The electrochemical properties of the solvent, and the colloidal suspension formed using the solvent, also can be dependent on handling, i.e., shaking, which can result in vibrations that produce more electrostatic charge separation of the virus particles. The electrochemical properties of the solvent and the colloidal suspension also can be dependent on environmental factors such as the temperature of the solvent or the suspension. Therefore, to eliminate ambigu-ous or erroneous results due to changes in temperature and other environmental factors, the system 10 uses a two-chamber analysis technique in which one liquid-filled cham-ber is used as a reference, and the other liquid-filled chamber contains the colloidal suspension of entrapped sampled particles, i.e., the sample medium. More specifically, as shown in FIG. 1, the system 10 further comprises a reference chamber 30 containing the solvent with no dispersed virus particles, referred to hereinafter as a "reference medium;" and a sample chamber 32 containing the colloidal suspen-sion of the virus particles and the solvent, i.e., the sample medium. Alternative embodiment of the system 10 can have a single-chamber configuration, i.e., alternative embodi-ments can be configured without the reference chamber 30 and can forgo the use of a reference medium.

As noted above, the thoracic and respirable fractions, upon being separated from the air sample in the aerosol sampler, are absorbed into a solvent in the form of a liquid medium, or a gel-like solid or semi-solid medium. Upon completion of the predetermined sampling period, the result-ing colloidal suspension, or sample medium, is transferred to the sample chamber 32. The reference chamber 30 contains the same solvent, in the same volume, as the sample cham-ber 32, but the solvent in the reference chamber 30 does not include any absorbed particles. The solvent in the sample chamber 30, i.e., the reference medium, otherwise is substantially identical to the sample medium.

Also, the reference medium in the reference chamber 30 is maintained at substantially the same environmental conditions, including temperature, as the sample medium in the sample chamber 32. The relevant properties of the reference medium, therefore, can act as a baseline against which changes of the conductivity of the sample medium can be evaluated. As discussed below, this technique helps to maximize the signal to noise ratio in the signal that ultimately is used as an indication of the viral load in the sample medium.

The two-chamber system 10 further includes a two-probe/four-electrode system to measure the relevant characteristics of the reference medium and sample medium in the respective reference chamber 30 and sample chamber 32. More specifically, the system 10 comprises a first conductivity probe 36 and an identical second conductivity probe 38, shown in FIGS. 1, 1B, and 5. The first conductivity probe 36 and the second conductivity probe 38 each include a positive electrode 39a and a negative electrode 39b. The electrodes 39a, 39b of the first conductivity probe 36 are immersed in the sample medium in the sample chamber 32. The electrodes 39a, 39b of the second conductivity probe 38 are immersed in the reference medium in the reference chamber 30. Single-chamber versions of the system 10, i.e., alternative embodiments of the system 10 that do not incorporate the reference chamber 30, can be configured without the second conductivity probe 38.

As discussed below, the first and second conductivity probes 36, 38 form part of a homodyne frequency detection circuit. The frequency responses of the first and second conductivity probes 36, 38 are proportional to the respective electrical conductivities of the sample medium and the reference medium. As discussed below, the system 10 is configured to determine the differential frequency response between the first and second conductivity probes 36, 38, and to estimate the viral load in the sample medium based on the differential frequency response.

Figure 5:
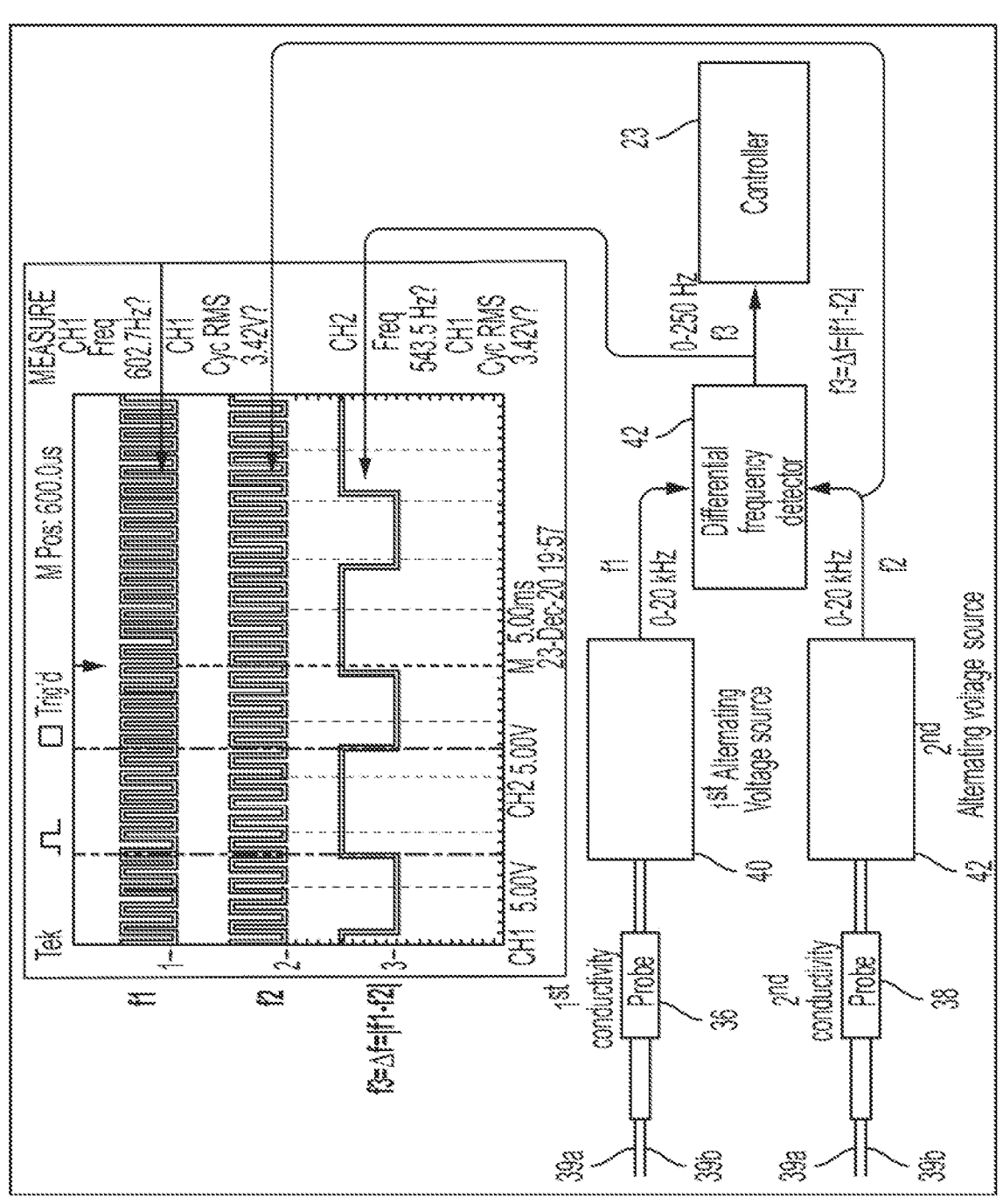
FIG. 5 is a diagrammatic illustration of various electrical components of the system shown in FIGS. 1-1B and 3A-4E, with a graphical representation of various frequency measurements made using the components.

The system 10 also comprises a first alternating frequency generator 40, a second frequency generator 41, and a differential frequency detector 42, also shown in FIGS. 1 and 5. The first frequency generator 40 is communicatively coupled to the first probe 36, and to the differential frequency detector 42. The second frequency generator 41 is communicatively coupled to the second probe 38, and to the differential frequency detector 42. The first and second frequency generators 40, 41 each generate a sinusoidally-varying voltage that produces an alternating electrical potential across the positive and negative electrodes 39a, 39b of the respective first and second conductivity probe 36, 38 (activities 108a, 108b in FIG. 2A). The frequency of the voltage is characteristic of the RC (resistance/capacitance) of the alternating current (AC) circuit driving the alternating voltages. Single-chamber versions of the system 10 can be configured without the second frequency generator 41 and the differential frequency detector 42.

The electrical potential across the positive and negative electrodes 39a, 39b causes an alternating current to flow between the positive and negative electrodes 39a, 39b via the sample medium or the reference medium in which the respective first and second electrodes 39a, 39b are immersed. The frequencies of the alternating currents are related to the respective electrical conductivities of the sample and reference media. The sample medium, i.e., the colloidal suspension in the sample chamber 32, is polarized due to the presence of virus particles, such COVID-19 virus particles, that have spike proteins, since the presence of the spike proteins results in an electrostatic charge. Thus, the electrical conductivity of the sample medium is related to the presence, or absence, of virus particles in the sample medium.

The first and second frequency generators 40, 41 each produce a sinusoidal output signal having a frequency approximately equal to the frequency of the alternating current flowing through the respective first and second probes 36, 38. The output signals are transmitted to the differential frequency detector 42. The differential frequency detector 42 determines the frequency difference between the signals using a homodyne detection technique (step 110 in FIG. 2A). The differential frequency detector 42 can determine the frequency differential, using a heterodyne detection technique, in alternative embodiments. The differential frequency detector 42 generates an output representative of the frequency differential, and sends the output to the controller 23. The differential frequency detector 42, the first and second frequency generators 40, 41, and the first and second probes 36, 38 thus constitute a homodyne frequency detection circuit. As discussed below, the frequency differential is processed to estimate the amount of virus particles in the sample medium within the sample chamber 32.

As noted above, the frequency of the alternating current flowing between the first and second probes 36, 38 and the respective first and second alternating frequency generators 40, 41 is related to the electrical conductivities of the respective sample and reference media in which the first and second probe 36, 38 are immersed; and the conductivity of the sample medium is related to the presence, or absence, of virus particles in the sample medium. Therefore, the frequency of the output signal generated by the first alternating frequency generator 40, i.e., the frequency response of the first probe 36 to the alternating voltage applied thereto, is related to the amount of virus particles in the sample medium.

The reference medium in the reference chamber 30 is substantially free of virus particles, and is maintained at substantially the same environmental conditions as the sample medium in the sample chamber 32. Therefore, the frequency of the output signal generated by the second frequency generator 41, i.e., the frequency response of the second probe 38 to the alternating voltage applied thereto, represents a baseline reference against which the effects of the any virus particles in the sample medium can be evaluated. By generating a signal representing the frequency difference between the respective frequency responses of the first and second probes 36, 38, and using the difference to determine the presence or absence of virus particles in the sample chamber 32, small changes in the frequency of the current through the first probe 36, in effect, are amplified, as can be seen in FIG. 5. This amplification, in turn, improves the signal to noise ratio in the output signal generated by the differential frequency detector 42, i.e., in the signal that ultimately is used to determine the presence and magnitude of the viral load in the sample medium.

The frequency response of the homodyne frequency detection circuit formed by the differential frequency detector 42, the first and second frequency generators 40, 41, and the first and second probes 36, 38 is proportional to the respective electrical conductivities of the sample and reference media. Also, the virus particles become electrically polarized upon being suspended in the solvent, causing the characteristic frequency of the sample medium to change monotonically with the viral load, i.e., the number of virus particles, in the sample medium. Thus, by determining the temporal and (optionally) the differential changes in the conductivity of the solvent in the sample medium resulting from the introduction of the virus particles thereto, the frequency response of the homodyne circuit can be correlated with the amount of virus particles in the sample medium. The amount of virus particles in the sample medium, in turn, can provide an indication of the viral load in the airspace from which the virus particles were sampled.

The output signal generated by the differential frequency detector 42, which represents the output of the homodyne frequency detection circuit, is transmitted to the controller 23, which in turn transmits the signal to the edge cloud server 46 via the wireless gateway 52. The output signal is processed to determine the presence, and amount of viral load in the sample medium within the sample chamber 32. In particular, the edge cloud server 46, in this particular aspect of its functionality, acts as a signal processing system that estimates the viral load in the sample medium by correlating viral load in the sample medium with the frequency response of the homodyne frequency detection circuit, as measured by the differential frequency detector 42. More specifically, the frequency response of the of the homodyne frequency detection circuit is correlated with a predetermined relationship between the frequency response and the viral load (step 112 in FIG. 2A). The predetermined relationship is generated by an initial calibration process in which the frequency response is evaluated in the presence of varying amounts of virus particles in the sample medium within the sample chamber 32.

The presence and magnitude of the viral load in the airspace from with the sampled virus particles were obtained can be estimated based on the viral load detected in the sample medium based, for example, on the sampling time during which the ambient was drawn into the particle collector 24 by the fan 22; the efficiency of the particle collector 24 at removing the particles of interest from the ambient air; the volume of air drawn through the particle collector 24 during the sampling period; etc. (step 114).

The calculation of the viral load in the sample medium, and the determination of the presence and magnitude of the viral load in the sampled airspace, can be performed by the edge-cloud server 46. Alternatively, the calculation of the viral load in the sample medium, and the determination of the presence and magnitude of the viral load in the sampled airspace can be performed by other types of computing devices including, without limitation, the controller 23 itself.

As noted above, alternative embodiments of the system 10 can be configured without the reference chamber 30, the second conductivity probe 38, the second frequency generator 41, and the differential frequency detector 42; and such embodiments can forgo the use of a homodyne or heterodyne frequency detection technique to determine a frequency-response differential between conductivity probes immersed in reference and sample media. In such embodiments, the viral load in the sample medium can be estimated solely from the temporal changes in the conductivity of the sample medium due to the presence of the virus particles.

The results of the air-sample analysis, i.e., viral load in the sampled airspace, can be subjected to an error-elimination process, discussed below (step 116 in FIG. 2A). Upon data acquisition from the sensors of the system 10, an edge-computation-based validation algorithm can be run to eliminate errors and verify the results of the air-sample analysis. If the obtained result is true of its nature, the result and corresponding monitoring statistics can be published locally, and on the edge-cloud server 46. In particular, if the results of the air-sample analysis are deemed valid, the results and other environmental data can be transmitted to, and displayed and/or stored on one or more display or storage devices (step 118). For example, the system 10 can include a visual display 51 communicatively coupled to the controller 23 by a wired or wireless means. The viral load determined by the system 10 can be displayed on the display 51. A safe social distance, calculated by the edge-cloud server 46 based on the viral load and other environmental factors, also can be displayed. A technique for calculating the safe social distance is described below.

Environmental data such as the ambient $CO_2$ level, PM concentration, air temperature, and relative humidity also can be displayed on the display 51. Other information, such as a plot of the airborne viral load over time, also can be displayed. If the validated viral load is above a safe level, a warning message, such as "High Viral Load Detected. Please Use Proper Safety Precautions and Air Purification" also can be displayed.

The wireless gateway 52 facilitates communication between the controller 23, the edge-cloud server 46, and other devices on which the air-sampling results, environmental data, and warnings can be displayed, processed, and/or stored. For example, the above noted information displayed on the display 51 also can be displayed on the smart phone 54 or the desktop computer 56. Also, data can be further processed and/or stored on a local server or a cloud server (not shown). Communication between the wireless gateway 52 and the above-noted devices can be facilitated by any suitable means, such as the internet, a cellular network, Wi-Fi, a local area network, a wide area network, BLUETOOTH, etc.

The system 10 can be further configured so that, upon the detection and validation of a high viral load, the system 10 immediately generates warnings and notifications cautioning recipients to take adequate precautions, such as leaving the area, to reduce the potential for viral exposure and possible infection (step 120 of FIG. 2A). For example, the system 10 can be configured to send such warnings and notifications to pre-designated recipients by way of e-mail or SMS (text) messaging. In one possible application, and without limitation, the pre-designated recipients can include the normal occupants of a particular floor of an office building on which the system 10 is used to monitor air quality.

The system 10 also can be configured so that, upon the detection and validation of a high viral load, the system 10 generates a command that activates an air filtration, disinfection, or ventilation system (not shown) that services the airspace in which the viral load have been detected (step 122).

The system 10 further can include a visual alerting device in the form of one or more LED displays 58, shown in FIG. 1. The LED displays 58 are communicatively coupled to the edge-cloud server 46, and can be placed in locations where they can be seen easily by occupants within the space being monitored by the system 10. Upon receiving an input from the edge-cloud server 46 that a high viral load or other alarming condition exists, the LED displays 58 illuminate, thereby providing a visual indication to those in the vicinity of the LED displays 58 that the viral load in the local space is at, or is approaching an unsafe level (step 124).

The system 10 further can include an audible alerting device in the form of one or more buzzers 60, depicted in FIG. 1. The buzzers 60 are communicatively coupled to the edge-cloud server 46, and can be placed in locations where they can be heard easily by occupants within the space being monitored by the system 10. Upon receiving an input from the edge-cloud server 46 that a high viral load or other alarming condition exists, the buzzers 60 emit an audible sound such as a pulsing buzzing noise, thereby providing an audible indication to those in the vicinity of the buzzers 60 that the viral load in the local space is at, or is approaching an unsafe level (step 126). The audible alert provided by the buzzers 60 can be particularly helpful when the user of the system 10 is not attentive to the visual alert provided by the LED displays 58.

The above warning and notification processes can be initiated by other computing devices, such as the controller 23, in alternative embodiments.

Figure 6A:
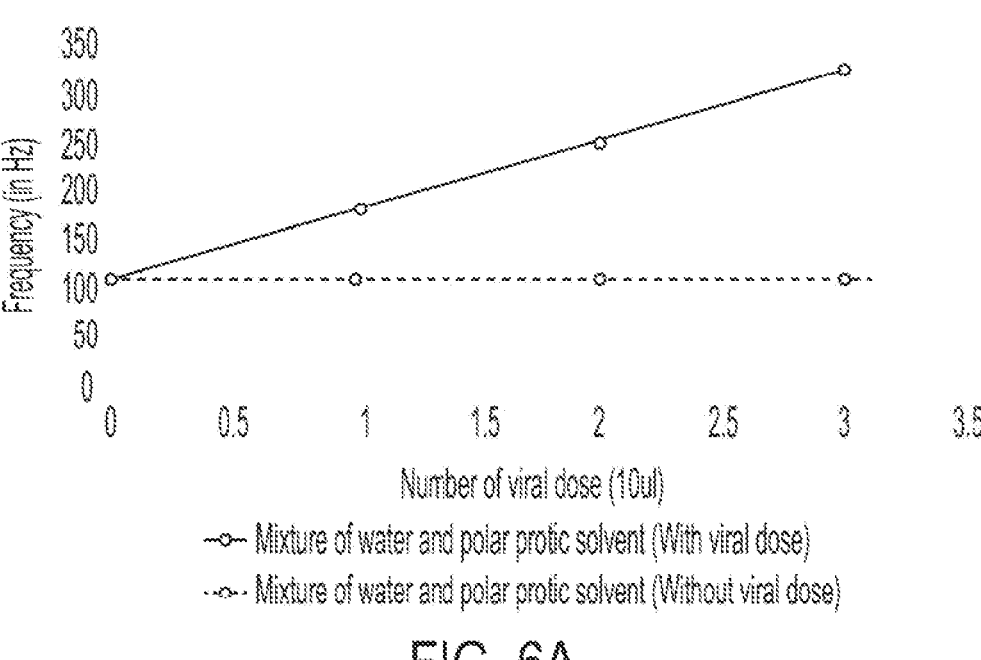
FIG. 6A is a graph depicting the relationship between the frequency of an alternating current through a first conductivity probe of an embodiment of the system shown in FIGS. 1-1B and 3A-5, as a function of the viral load in a medium in which the probe is immersed.
Figure 6B:
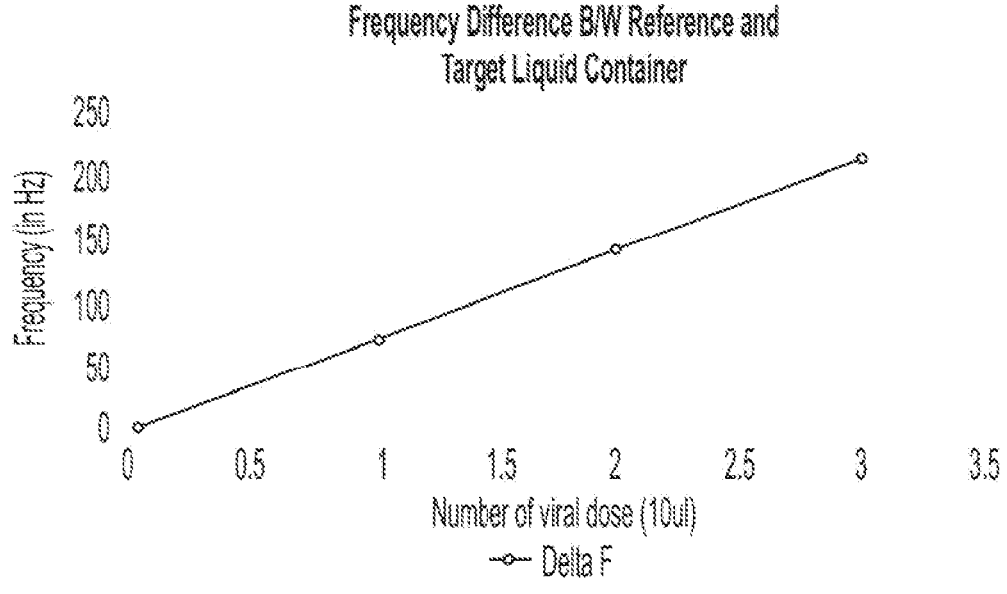
FIG. 6B is a graph depicting the difference between the alternating current frequency depicted in FIG. 6A, and the frequency of an alternating current through a second conductivity probe immersed in a medium that does not contain a viral load, as a function of the viral load in which the first probe is immersed.

An embodiment of the system 10 was tested with different polar aprotic solvents with distilled water, double deionized water, and a solution of pure water with slightly basic salts. The frequencies of the respective AC currents passing through the probes immersed in the sample and reference media were recorded with every viral dosage. The virus selected for the testing was a live attenuated MMR (measles, mumps and rubella) vaccine, at a concentration of 140 viral particles per 10 µL. As can be seen in FIG. 6A, the frequency of the output of the sample probe increased linearly as the viral load was increased. As can be seen in FIG. 6B, the difference between the output frequencies of the sample probe and the reference probe likewise increased linearly as the viral load was increased. The testing also was conducted using polio and rotavirus live attenuated vaccines; and similar frequency responses were found using these viruses. Depending on coronal spike structure of the different virus particles, and their timing in the air and the manner in which the particles interface with water droplets, each type of virus particle will generate different level of Zeta potential and Debye radius. Therefore, the system 10 relies on an advanced adaptive signal processing technique of comparing the response of the sample probe with a time series of baseline data to predict whether there is a burst of viral activities in the monitored airspace.

Figure 7:
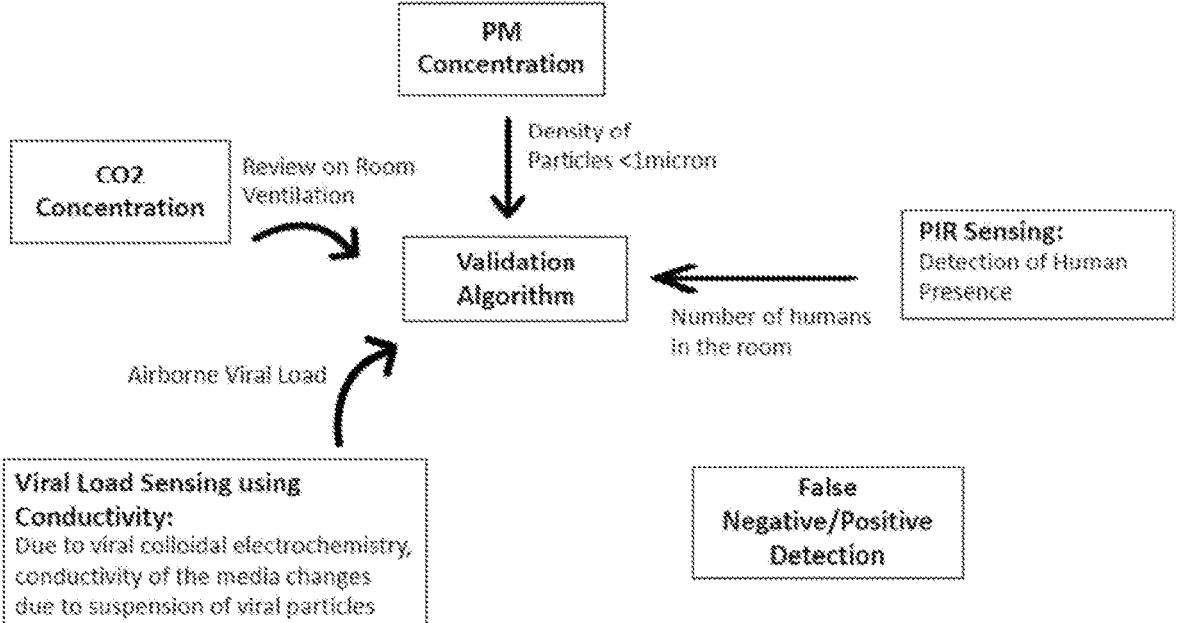
FIG. 7 is a block diagram of a validation, or error-elimination, process that can be performed by the system shown in in FIGS. 1-1B and 3A-5.

Referring to FIG. 7, the error-elimination process can be performed using a sensor-based validation approach that employs a validation, or error elimination algorithm stored on, and executed by the edge-cloud server 46. The validation algorithm can be stored on and executed by a different computing device, such as the controller 23, in alternative embodiments. The error-elimination process is based on inputs such as the carbon dioxide ($CO_2$) level in the space from which the sample was obtained; the particulate matter (PM) concentration and distribution within the space; and the presence or absence of people in the space.

The carbon dioxide concentration and the particulate matter concentration can be obtained from a respective carbon dioxide sensor 62 and particulate matter sensor 64, depicted in FIG. 1. The presence and/or number of persons in the space can be evaluated based on inputs from one or more proximity sensors or motion detectors 86. The carbon dioxide sensor 62, particulate matter sensor 64, and proximity sensors or motion detectors 86 can be communicatively coupled to the edge cloud server 46 by way of the wireless gateway 52, as illustrated in FIG. 1.

Referring again to FIG. 7, the $CO_2$ level, PM concentration, and the presence or absence of people are factors that can indicate the likelihood that an airborne virus is present in a particular space. For example, a relatively low level of carbon dioxide, e.g., about 400 ppm or less, and/or a relatively low particulate level, e.g., about ten ug/m³ (micro grams per cubic meter) or less, in the presence of one or more people in the space is an indication that the space has effective ventilation, which in turn is interpreted an indication that the likelihood of a significant viral load in the space is low. The absence of any people in the space likewise is interpreted an indication that the likelihood of a significant viral load in the space is low. Thus, if the system 10 generates an output indicating an unacceptably high viral load under such circumstances, the output is interpreted as a false positive, i.e., the result is considered invalid. The suspect result can be ignored, and if desired, the user can initiate another sampling cycle.

Conversely, a relatively high level of carbon dioxide, e.g., about 420 to about 450 ppm or greater, and/or a relatively high particulate level, e.g., about 50 ug/m³ to about 100 ug/m³ or greater, in the presence of one or more people in the space is an indication that the space has poor ventilation, which in turn is interpreted an indication that the likelihood of a significant viral load in the space is high. Thus, if the system 10 generates an output indicating an acceptably low viral load under such circumstances, the output is interpreted as a false negative, i.e., the result is considered invalid. The suspect result can be ignored, and if desired, the user can initiate another sampling cycle.

Figure 8:
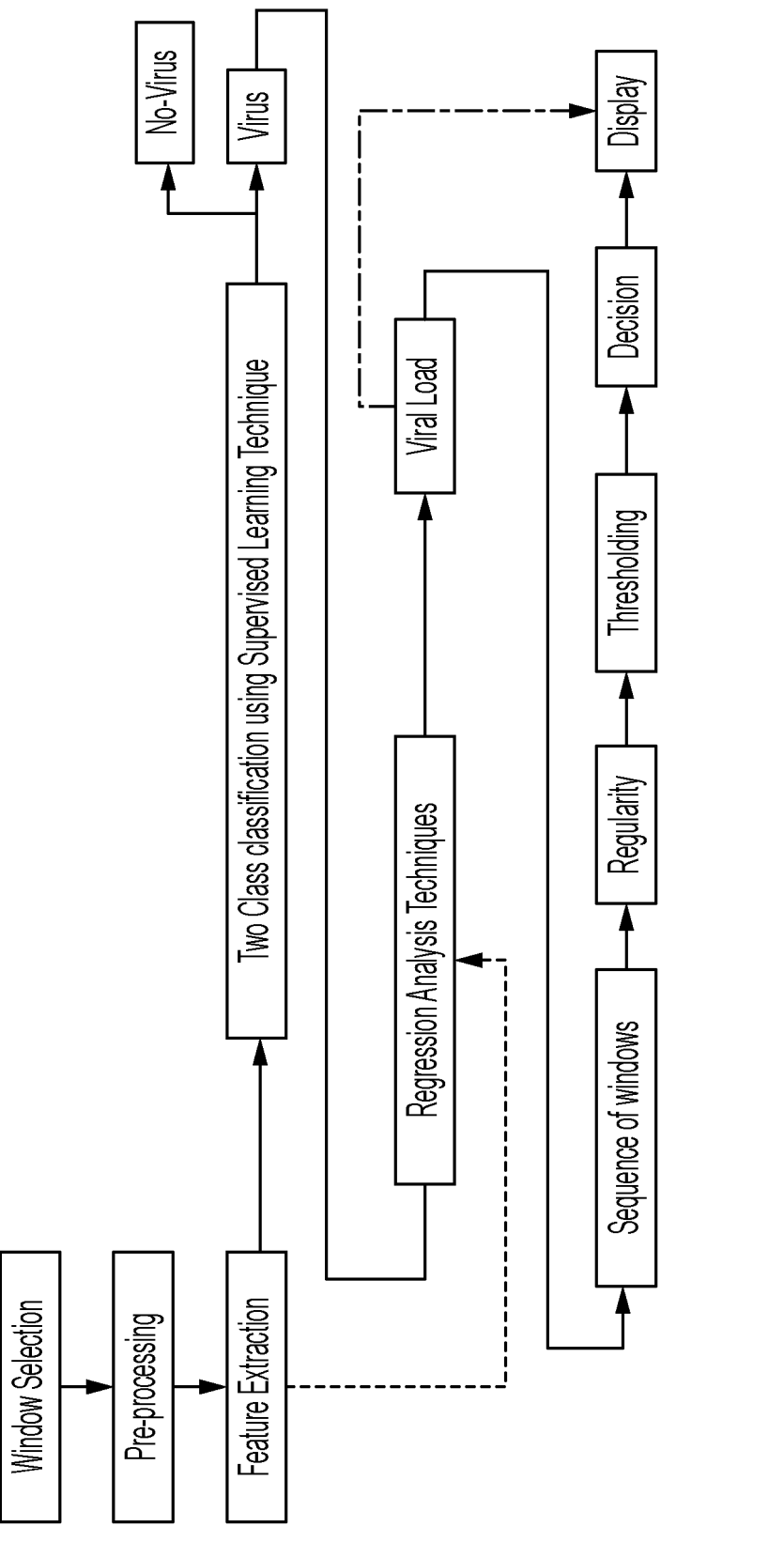
FIG. 8 depicts a validation, or error-elimination algorithm that can be used to perform an alternative validation process to the validation process depicting in FIG. 7.
Figure 9:
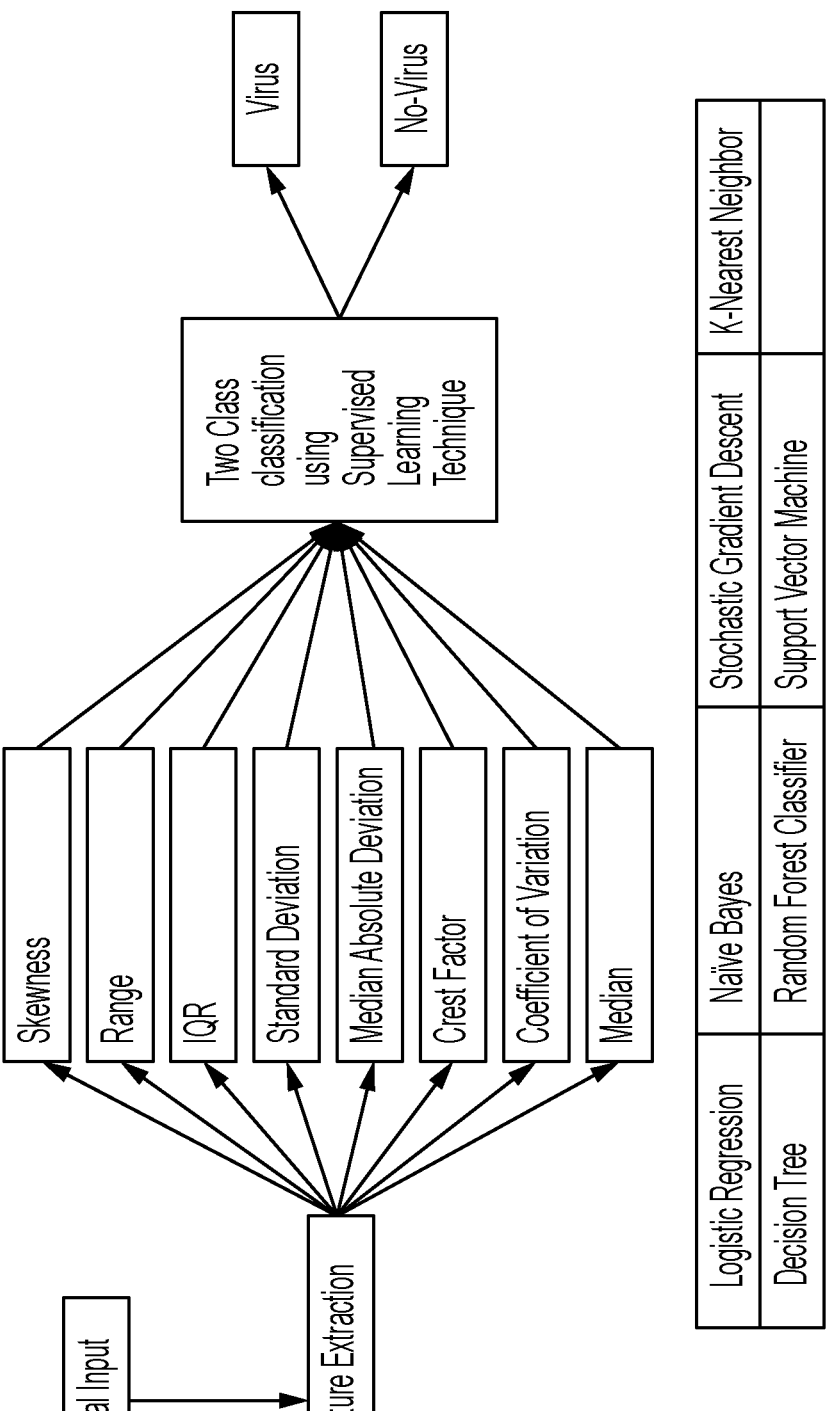
FIG. 9 depicts various statistical parameters used by the validation algorithm depicted in FIG. 8.

Alternatively, or in addition to the above-noted sensor-based validation approach, the error-elimination process can be performed using a signal-analytics-based approach that employs an additional error-elimination, or validation algorithm depicted in FIG. 8. The validation algorithm correlates signal artifacts, such as skewness, coefficient of variation, variance, etc. with the presence or absence of a viral load in the sample medium, to help eliminate false positive or false negative indications of a viral load by the system 10. The validation algorithm depicted in FIG. 8 can be stored on, and executed by the edge-cloud server 46. The validation algorithm can be stored on and executed by a different computing device, such as the controller 23, in alternative embodiments As can be seen in FIG. 8, the validation algorithm is developed by conducting pre-processing of the output signal received from the differential frequency detector 42; followed by feature-extraction, and the use of a supervised machine learning technique to develop a two-class classification algorithm that determines whether a viral load is or is not present based on one or more of the signal artifacts. FIG. 9 includes a non-exclusive listing of various statistical parameters, i.e., different signal artifacts, can extracted from the output signal and correlated with the viral load, to help maximize the accuracy of the validation process under different settings and conditions. FIG. 9 also includes a non-exclusive listing of various machine-learning techniques that can be used to develop the two-class classification algorithm.

Referring again to FIG. 8, the validation algorithm also incorporates a regression analysis technique to generate an algorithm for estimating the magnitude of the viral load, if one is present, based on the statistical parameters extracted from the output signal. As also can be seen in FIG. 8, once the magnitude of the viral load has been estimated, the validation algorithm can determine whether the magnitude exceeds a threshold indicating a high or otherwise significant viral load.

As an example, the technology disclosed herein was used with different engineered media to detect pseudovirions for SARS Cov-2 with s-spike protein. A validation process as depicted in FIG. 8 was performed on the results, and the results of the validation process are shown in FIG. 10.

After the viral load has been verified by one or both of the above validation techniques, the frequency-based conductivity signal, i.e., the output signal received from the differential frequency detector 42, and the estimated viral load can be communicated to one of more of the various display and alert devices discussed above and depicted in FIGS. 1 and 11, by way of the wireless gateway 52.

The edge-cloud server 46 can be configured to determine the minimum social distance, based on the environmental conditions in the space being monitored. In particular, the edge-cloud server 46 can be programmed with algorithms that, when executed by the edge-cloud server 46, calculate the minimal social distance at a given time based on the measured temperature and humidity of the ambient air; and the concentration and size distribution of particles in the ambient air.

It is believed that the size of the droplet nuclei resulting from sneezing, coughing, and talking is a function of the process by which the droplets are generated, and the environmental conditions. For example, sneezing can generate around 40,000 droplets in the about 0.5 micron to about 12 micron range, which most likely are aerosolized. Also, studies have shown that talking for five minutes can generate the same number of droplet nuclei as a cough, i.e., about 3,000 droplet nuclei. The actual size distribution of the droplets is dependent on parameters such as the exhaled air velocity, the viscosity of the fluid, and the flow path.

Human-to-human transmission of pathogens such as the COVID-19 virus takes place via droplets, or aerosol transportation, from one individual to another. After being exhaled by an infected person, respiratory droplets with various sizes travel and simultaneously evaporate in the ambient air. The droplets begin to exchange heat and mass with the ambient air while moving under the influence of various forces such as gravity, buoyancy, and air drag. It is believed that the respiratory droplets evolve into two categories, large and small-sized droplets, depending on their initial diameter. Large-sized droplets can reach limited distance, whereas small-sized droplets dry to form a cloud of aerosol particles that can remain suspended in the air for a significant amount of time.

The time of flight and distance traveled by exhaled particles depend upon the transport characteristics of the ambient air, i.e., the viscosity, temperature, specific heat capacity, and thermal conductivity of the ambient air. The transport characteristics vary with the ambient temperature and relative humidity, and hence can change the minimum social distance required to minimize the potential for person-to-person transmission of pathogens carried by exhaled particles. The following set of equations can be used to estimate the distance an exhaled particle will travel, using the temperature and relative humidity of the air through which the particle will travel, and the concentration of particles in the air:

$$
\begin{cases}
\dfrac{dr_p}{dt} = \dfrac{CM_v D_\infty p Sh}{\rho_p r_p R T_\infty} \ln\left(\dfrac{p - p_{va}}{p - p_{v\infty}}\right) - f_1(r_p, T_p, \vec{V}_p) \\[2ex]
\dfrac{dT_p}{dt} = 3K_g \dfrac{(T_\infty - T_p)}{c_p r_p^2} Nu - \dfrac{L_v I}{m_p c_p} - \dfrac{3\Gamma(T_p^4 - T_\infty^4)}{r_p c_{-p}} = f_2(r_p, T_p, \vec{V}_p) \\[2ex]
\dfrac{d\vec{V}_p}{dt} = \vec{g}\left(1 - \dfrac{\rho_p}{\rho_g}\right) - \dfrac{3C_d \rho_g |\vec{V}_p - \vec{V}_g|(\vec{V}_p - \vec{V}_g)}{8\rho_p r_p} f_3(r_p, T_p, \vec{V}_p) \\[2ex]
\dfrac{d\vec{x}_p}{dt} = \vec{V}_p = f_4(\vec{V}_p)
\end{cases}
=
$$

Because the minimum social distance is related to the distance an exhaled particle will travel, the above equation set can be used to estimate the minimum social distance based on the ambient temperature and relative humidity, and the particle concentration in the ambient air.

The parameters used in the above equation set are air transport characteristics at different temperatures and different relative humidity (RH) values, where:

$$r_p = \text{Radius of the droplet}$$

$$T_p = \text{Temperature of the droplet}$$

$$V_p = \text{Velocity of the droplet}$$

$$X_p = \text{Distance traveled by the droplet}$$

The edge-cloud server 46 is configured to perform a Runge Kutta Fourth Order Method to solve the above differential equations for the distance traveled by the droplet under the specific conditions existing at a particular time. The distance traveled by the droplet represents the minimum separation distance for that particular point in time.

Figure 13:
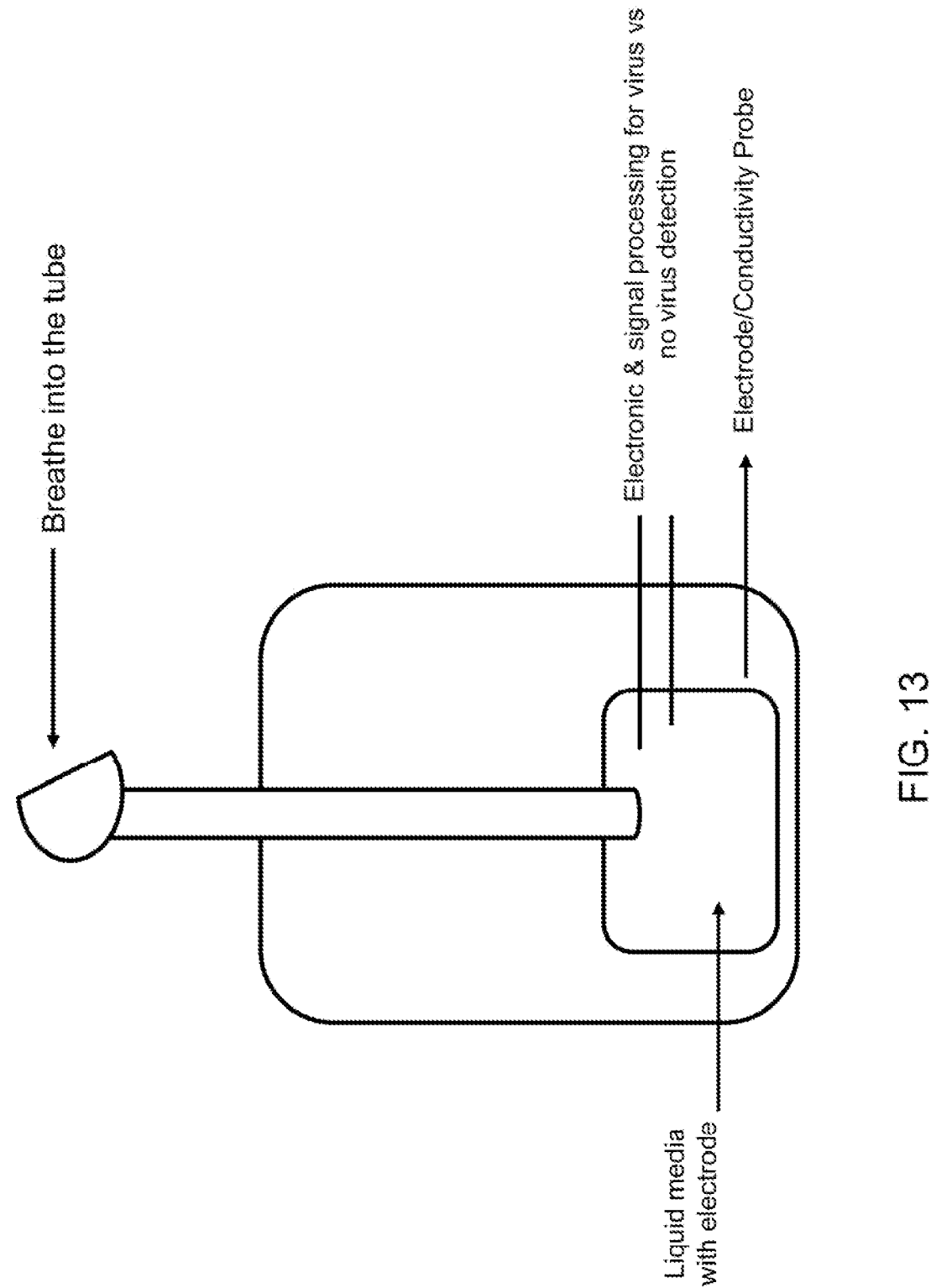
FIG. 13 is a diagrammatic representation depicting an alternative embodiment of the system shown in FIGS. 1-1B and 3A-5.

FIG. 13 is a diagrammatic representation depicting an alternative embodiment of the system 10. The alternative embodiment comprises a tube, such as the type of tube used in breathalyzer machines, in fluid communication with a sample chamber holding a solvent. A user can breathe into the tube. If the user is infected with a virus, such as the COVID-19 virus, this action will result in the introduction of virus particles into the sample chamber, and the deposition and suspension of the virus particles in the solvent. The alternative embodiment can detect the presence of the virus particles in the manner described above in relation to the system 10.

Figure 14:
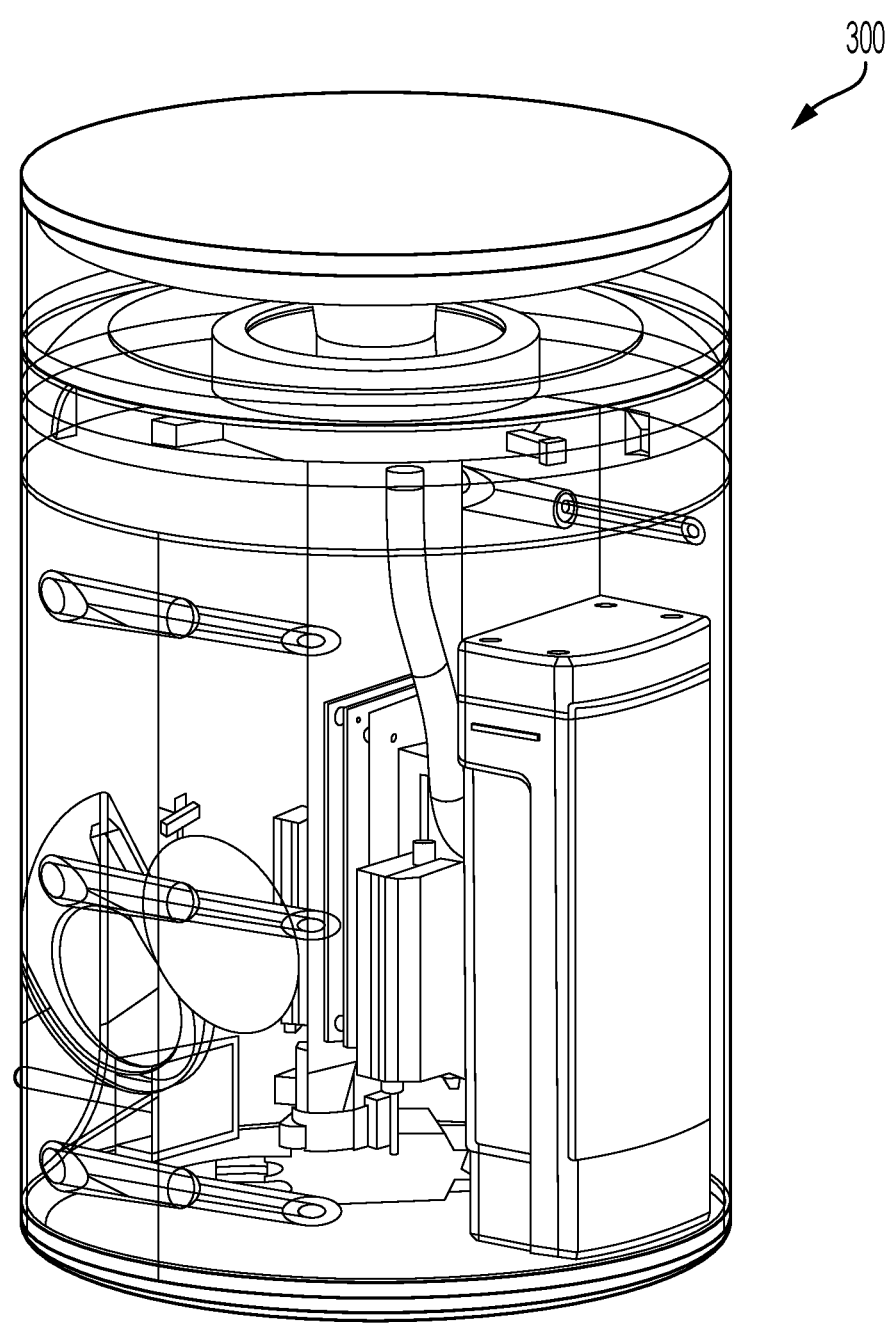
FIG. 14 is a top-side perspective view of another alternative embodiment of the system shown in FIGS. 1-1B and 3A-5.

An alternative embodiment of the system 10 in the form of a system 300 is depicted in FIG. 14. The system 300 is configured to detect the target viruses as exhaled from infected people nearby without requiring immediate adjacency.

The system 300 comprises a driver in the form of a "pancake" that can be, for example, about 1.20 mm in diameter and about 25 mm thick. The driver is a reverse-curve centrifugal fan, which provides high static pressure (suction) for its size. The fan (driver) can move up to, for example, about 58 cubic feet per minute (CFM) of air, and can achieve a static pressure of up to, for example, about 0.57 inches of water with a 4.12-inch diameter inlet flow of 0.9 feet per second (FPS) (27 cm/sec), and a noise level of not more than about 51 dBA.

In alternative embodiments, the system 300 can be configured with a series resistor or fans with coils tailored to slow the fan speed to about 27 CFM for a static pressure of about 0.34 inches of water and a noise level that can be brought below about 40 dBA at 1 meter. This will reduce the inlet flow to about 12-13 cm/sec.

The fan is placed horizontally at the top of a main housing body of the system 300. The fan draws air downward, and natively homogenizes the incoming air. The outlet airflow of the fan is radially outward, in a full circle.

The top section of the structure above the fan incorporates a passive lateralizer that enhances the sidewise airflow down into the fan's inlet, at the expense of the downward airflow from directly above. The downward stalk of the lateralizer is centered over the fan's inlet; the lateralizer is supported by struts from beyond the fan's housing; and a vertical mesh ring safeguards the inlet.

The horizontal radius of impact of the suction draw, i.e., the reduced static pressure, provided by the fan, and therefore, by the system 300, is determined empirically by measuring the distance from its center at which it manifests an inward airflow of at least about 10 cm/second.

The radial output of the fan is divided by a turban-like flow diverter, which divides the fore and aft sections of the fan's circumference to provide a measured airflow of about 5-6 cm/sec (10-12 fpm) to a testing chamber within the front replaceable chamber unit. The balance of the incoming airflow travels to an aft exhaust air collection hollow.

The rear, i.e., the most inward, of the pocket hollows is extended by about 0.8 inch to include a rear "closet" chamber hidden by a well-fit cover lid that attaches using tamper-resistant screws. The main printed circuit board (PCB) is the most forward element behind the lid, and it may support top and bottom cable feeds to other areas. At the true back wall of the pocket, the FR4 plain side of a single-sided copper-clad raw printed circuit board (with the copper facing the back wall is grounded to act as a Faraday shield element) connects through the true back wall. On the other side of the wall, a second and identical section of board is mounted, copper side facing the wall, as another shield element.

The main PCB can be located toward the lower end of the "closet," to allow for the air inlet and outlet vent tubes to cross above. Cabling, such as shielded multiconductor cabling, connects the main PCB to the "fingers" PCB that interfaces with the test chamber cap, to the alphanumeric display, to the eight 8 by 8 lidar sensors, to an IR emitter, to the various interlocks, to the power supplies, and to a relay control for the ballast.

Air vent tubes connect the test chamber inlet to the apportioned forward circumference, mating at a rubber seal with a downward-curved tube inside the test chamber. Similarly, an upward-curved tube provides an outlet that feeds air exhausted from the test chamber into the rear collection hollow. Custom molds for vent tubes on both sides of the rear wall of the front replaceable test chamber unit can allow that transition to be a single rectangular hole at that rear wall connecting round vent tubes on both sides of that wall.

The rear collection hollow houses a vertically oriented, U-shaped UVC lamp with 5.5 Watts of UVC power to disinfect the collected air. The collected air exits through a notched recess at the rear of the housing through a slanted port that, on the outside of the case, accepts a purpose-built 3-inch HEPA filter. A mechanical microswitch interlock electrically confirms the presence of the HEPA filter (in part as a UVC leakage prevention measure). The rear and downward-slanted air exit helps to prevent any surviving microorganisms in the exhaust from being inhaled by people located near the system 300. The filter slides into a bracket frame outside the vent port, and an inner edge gasket strip maintains its closure against the housing.

The rear collection hollow houses a vertically oriented, U-shaped UVC lamp with 5.5 Watts of UVC power to disinfect the collected air. The collected air exits through a notched recess at the rear of the housing through a slanted port that, on the outside of the case, accepts a purpose-built 3-inch HEPA filter. A mechanical microswitch interlock electrically confirms the presence of the HEPA filter (in part as a UVC leakage prevention measure). The rear and downward-slanted air exit helps to prevent any surviving microorganisms in the exhaust from being inhaled by people located near the system 300. The filter slides into a bracket frame outside the vent port, and an inner edge gasket strip maintains its closure against the housing.

UVC and Shielding

The system 300 can include a VW185.5-1 254-nm UVC lamp from Fulham. Like all fluorescent-derived gas discharge UVC lamps, the lamp generates constant electromagnetic output when operating, and this could impact the performance of the sensor probes. The system 300 includes multiple Faraday shields to reduce this potential impact.

The UVC lamp subassembly mounts about 1.5 inch to about 2 inches rearward of the PCB fastened to the "outside" of the aforementioned "closet," with the orientation of the lamp parallel with that plane. The lamp faces the rear vent, but a spaced polycarbonate panel blocks direct UVC exposure of the filter while allowing air to pass. The lamp itself is plugged into a 2G11 socket that, along with a metal center-of-U clip, mounts onto a rectangle of Anomet 254-nm-reflective aluminum, with the reflective side beaming additional UVC illumination toward the rear of the housing. A rectangular, single-sided RAW PCB is mounted onto the non-reflective side of the aluminum rectangle, with its copper side facing away from the aluminum.

Both the copper and the aluminum can be connected to ground, for two additional stages of Faraday shieling. The 2G11 cabling to the four wires of its ballast come up from the crawl space through a section, or "floor," located between the two PCBs and, therefore, shielded from UVC exposure.

The lamp tube is positioned at the center of the 10-inch by 3.5-inch rectangle of aluminum. The aluminum rectangle can be made of, for example, Anomet Anolux-MIRO IV-UVC with above 90 percent total reflectivity and easy-peel polyfilm, 0.020-inch by 10-inch by 3.5-inch, due to its slow degradation per 1,000 hours of UVC exposure. Anolux UVS with 84 percent can be use in the alternative. This can enhance both the shielding impact of the aluminum, and the reflected UVC radiance that increases the disinfection dosage to the air on its way to exit the exhaust chamber.

UVC Lamp/Reflector/Shield Subassembly

The lamp/socket/clip/aluminum/copper-clad-board stack is configured as a subassembly. The unit can have mount points to simplify its attachment (and connection) to the main assembly. Panels can be placed within the larger exhaust air collection hollow, to allow free air passage while blocking UVC emissions.

A reserved space, beneath the bottom of the HEPA port and in the same "crawl space" section where the power cord exits, houses DC supplies, such as a Mean Well SV 16 W for the PCB and displays, and another supply for the fan; and a Fulham SC-series "Sugar Cube" UVC ballast.

A high-density dot matrix message display, capable of displaying international character sets, is positioned at the top front of the system 300, above the section where the replaceable test chamber unit fits.

Eight individually-window-mounted person-detection lidar sensors are placed at eight "compass" points, in 45-degree intervals, in a horizontal ring around the unit. The sensors can be "tuned" to a detection distance that is about 25 percent to about 50 percent greater than the radius of impact of the inlet fan.

The system 300 also includes an opportunely positioned infrared (not human-visible but white to many video surveillance cameras) emitter, configured and driven to light for approximately four seconds in the event of a positive virus detection.

Any of several real and virtual interlocks can inactivate the system 300. Target circumstances for deactivation can include, for example:

Absence of a replaceable test chamber unit

Presence of a test chamber unit that has been user-refilled

Fluid depletion to 30% of fill height or less

Absence (or incomplete seating) of HEPA filter

Tilting to an extent that might allow spills of fluid into the main housing

Continuing agitation

Detection of spilled fluid within the main body of the device

User interface text messages can include, for example:

Hello

Monitoring . . .

Please wait—Recalibrating . . .

Alert! Contagious virus detected!

Alert! Influenza B virus detected!

Alert! SARS-Cov2 virus detected!

Fluid low—replace cartridge

Trouble code ##—see app/contact support

Invalid cartridge found—code ##

Service needed—contact support

Please wait—Updating

[Time) [Day) [Date]

Figure 15:
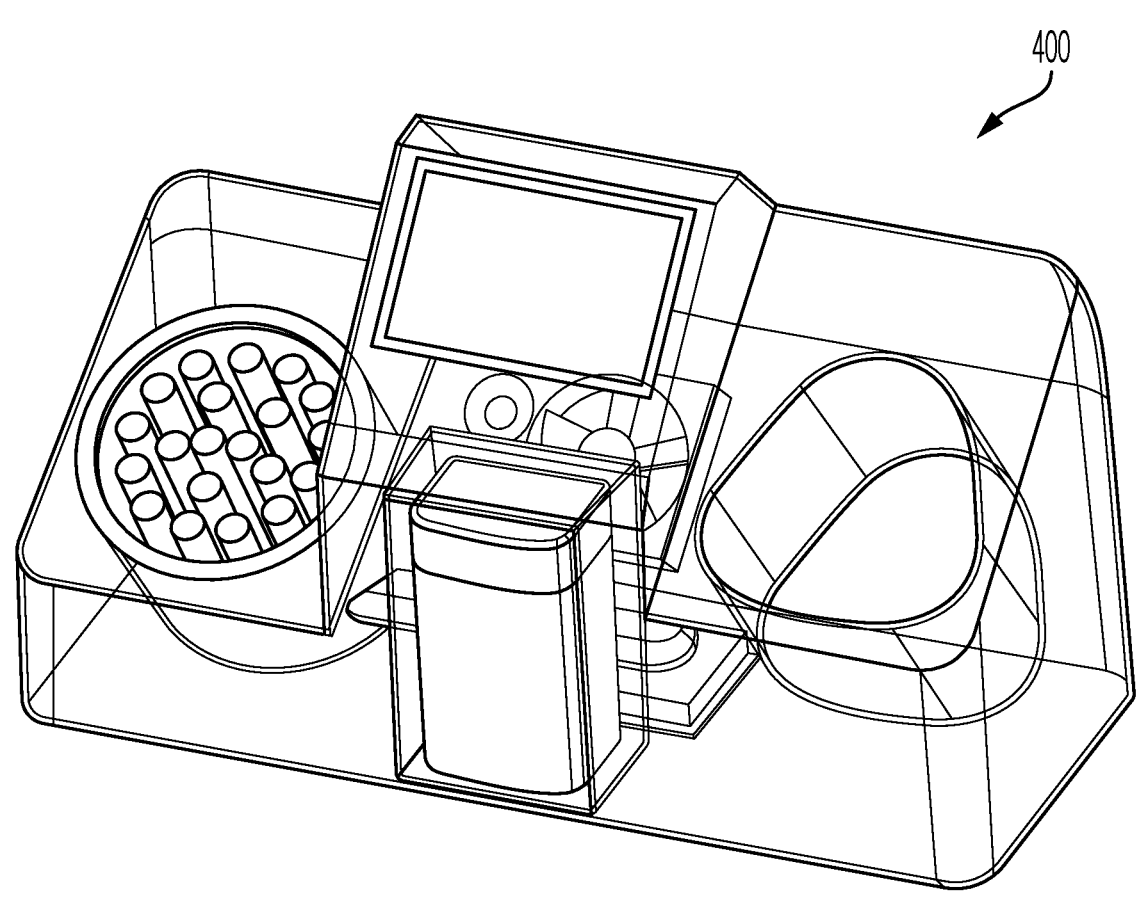
FIG. 15 is a perspective view of another alternative embodiment of the system shown in FIGS. 1-1B and 3A-5.

Another alternative embodiment of the system 10 in the form of a system 400 is depicted in FIG. 15.

The system 400 includes a horizontal housing that accepts a single-use blow tube into a mating-specific receptacle 404. A 5.7-inch display panel, about the size of a smart phone screen, provides step-by-step instructions through color illustrations and plain text, which may be displayed in an app-selected choice of language.

Blow tube replacement kits can include, for example, 100 individually wrapped blow tubes divided into four 25-piece packages, which is the fit size of a dispenser cup on the left side of the system 400; four sealed disposal cups which each fit into a corresponding hold on the right side of the system 400 and feature a sharps-disposal-type bladder on the lid; four sealable bags for holding one filled disposal cup each; four postpaid disposal return cartons; and a replacement HEPA filter.

The blow-tube supply cup, the blow tube entry port, and the blow tube disposal cup are each accompanied by a respective panel-mount LED that acts as a pointer, in conjunction with the on-screen illustration and illustration. The LED at the supply cup can be, for example, white or green; the LED at the blow tube inlet can be, for example, blue; and the LED at the disposal cup can be, for example, amber or white.

The replaceable test chamber has a relatively small volume, e.g., about four to about six ounces of the reference fluid; and slides into the bottom front of the housing.

Figure 16:
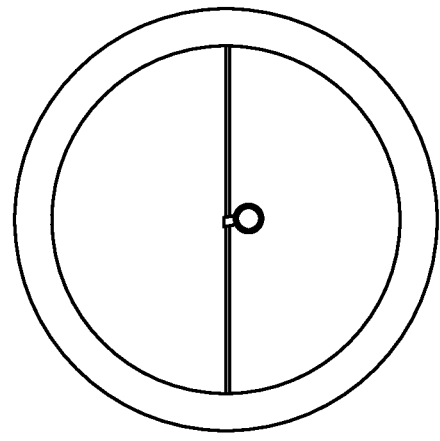
FIG. 16 is a top view of a blow tube inlet of the system shown in FIG. 15.

The blow tube inlet is shown in FIG. 16. The blow tube inlet is shaped like back-to-back capital "D" letters, with a bisected circle with a pin or tab dividing its center; and is sized to accept, for example, only ⅝-inch outside-diameter blow tubes that are slitted to straddle the divider. The inlet can be surrounded by a blue identifying ring and a small blue indicator LED placed adjacent thereto. The blue ring can be LED-backlit in alternative embodiments.

The single-use blow tubes each have, for example, a circular-cross section, a total length of about four inches, an outside diameter of about eight inches, and a six-inch deep "straddle" slot having a width sized to straddle the divider. The size and divider of the blow tube are configured to make intrusion by drinking straws, etc., difficult. The blow tube can be supplied individually wrapped.

The software of the system 400 can perform some, or all of the following functions:

1. Log the time and date of individual test cycles in nonvolatile memory as they occur.

2. Log the length of runtime for the UVC lamp.

3. Accept refill/resupply updates from the app.

4. Calculate the likely depletion of the blow tube supply in the unit.

a. Display an on-screen message if the app is not updating resupply events, e.g., more than 25 runs without an update.

i. If there has never been evidence of app usage, display a QR code to let a smart phone fetch the app.

ii. If there is evidence of prior app usage, display a message explaining how to update the supplies status within the app.

b. Use modulo-25 counts to determine when single-use 25/cup blow tube resupply requirement approaches (e.g., <S blow tubes remain)

c. Use modulo-100 counts to determine when to order a new 4 by 25 refill kit.

5. Monitor the pace of test cycle usage, e.g., events per day/week/year, average hours between events, etc.

The system 400 can further include a five-inch graphics and text display at the top center that can direct the user through all operations. The display can be located just above the blow tube inlet.

The internal section of the blow tube inlet includes a miniature mechanical switch to confirm the full insertion of a blow tube.

A vent tube directs the blown breath to the replaceable test chamber cartridge below. A Bosch BMP390 MEMS air pressure sensor monitors the strength of the blow within the vent, to determine if another blow is required. The exit vent port from the chamber empties into the internal chamber.

FIG. 16 is a below, assembled side view of the system 400, show the cartridge in its chamber (on the right); the blow tube holder cutaways; the horizontal UVC lamp above the ballast/DC supply level; the position of the HEPA filter and exhaust booster fan angles at the rear (the back housing notch is not depicted); and, above, display panel and blow tube inlet locations.

The system 400 also includes a UVC lamp positioned horizontally within the housing. The lamp is turned on for about 20 seconds following each test, to disinfect any remaining microorganisms within the housing, which is itself formed from an antimicrobial-treated polycarbonate-based plastic.

The system 400 further includes an externally-mounted, round, three-inch HEPA filter positioned in a 45-degree angled notch formed in the rear of the housing. The full insertion of the filter is monitored by a miniature mechanical interlock switch. The fan is mated to an internally mounted three-inch axial exhaust-booster fan. The fans turn on briefly, e.g., for about 30 seconds, as a last event once the after-test UVC disinfection illumination is complete.

The system 400 includes ST Microsystems VLS3LSCX lidar 8 by 8 array sensors that detect users approaching from the front of the device. The detection triggers a "Hello" display, followed by a circumstance-dependent sequence of displays and operations. These operations, which are presented in a language determined by the "Settings" choice within the app, are color-illustrated to help avoid user errors.

Instructions can include, for example, removing and unwrapping a new blow tube; holding the tube with the arrow on the tube and its slotted end pointing away from the user; confirming when the tube is properly inserted; notifying the user when the testing begins; indicating the outcome of the test (target virus detected or not detected); removing the used tube; inserting the used tube into the disposal case through a bladder; running a UVC disinfection cycle; exhausting disinfected air through the rear HEPA filter; thank you for using; ready for the next test; and the time/day/date.

Figure 17:
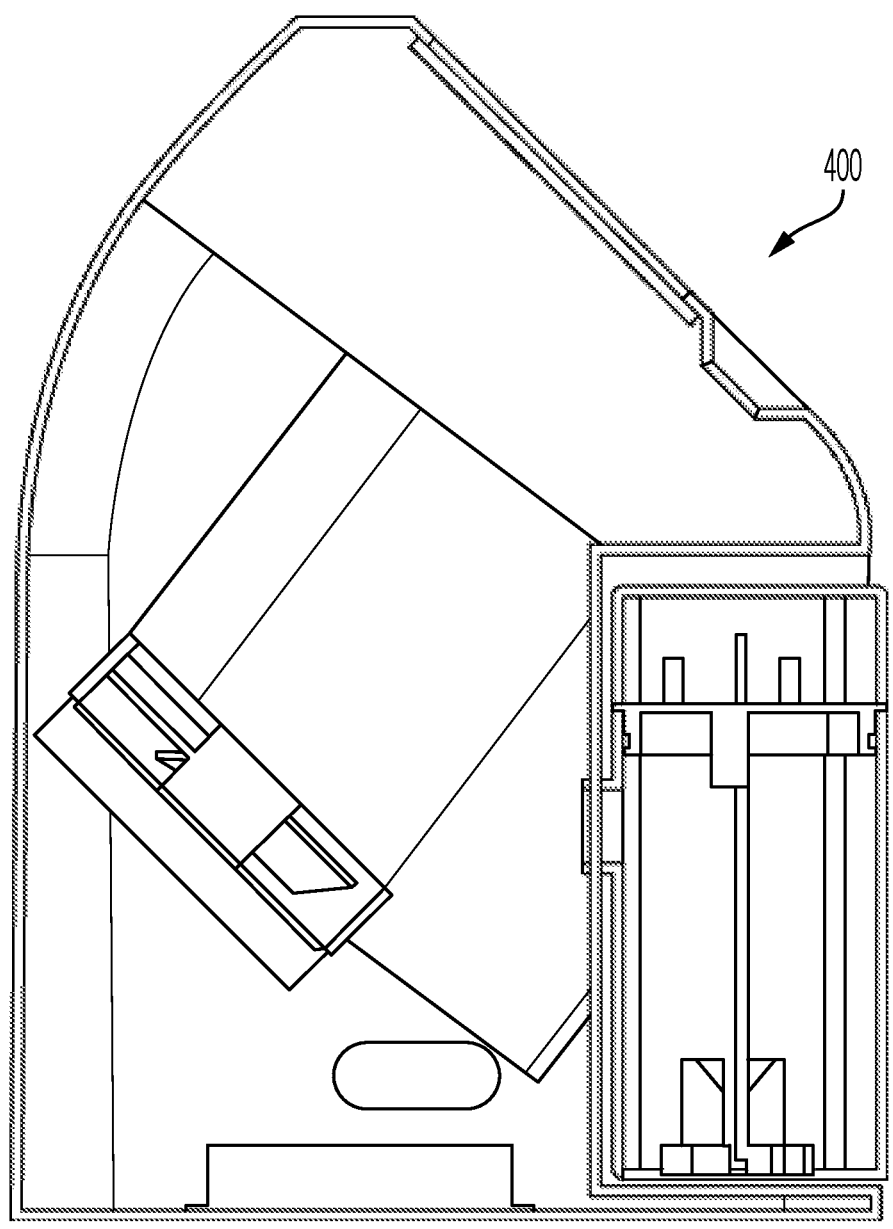
FIG. 17 is a side view of the system shown in FIG. 15
Figure 18:
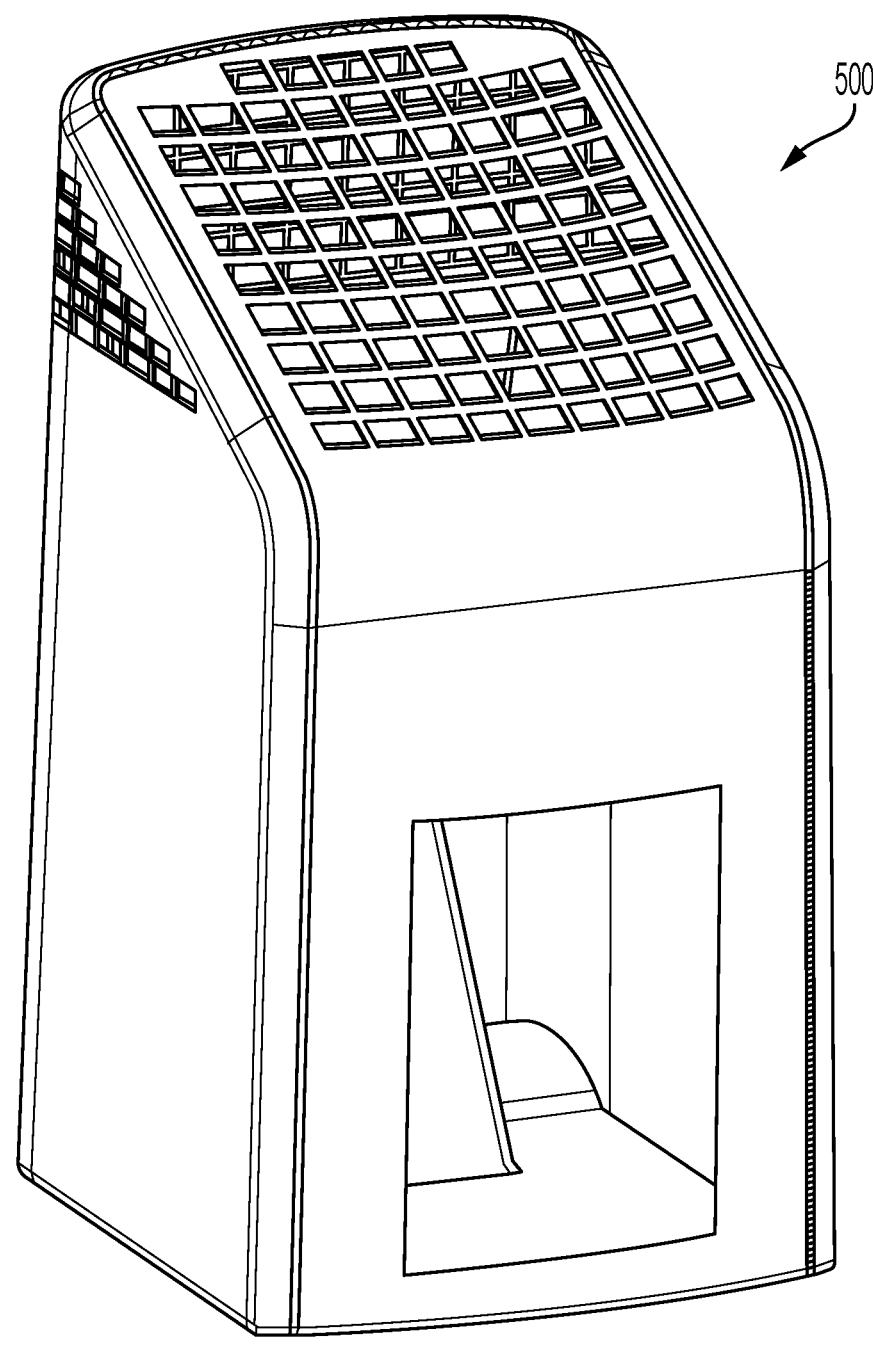
FIG. 18 is a perspective view of another alternative embodiment of the system shown in 1-1B and 3A-5.
Figure 19:
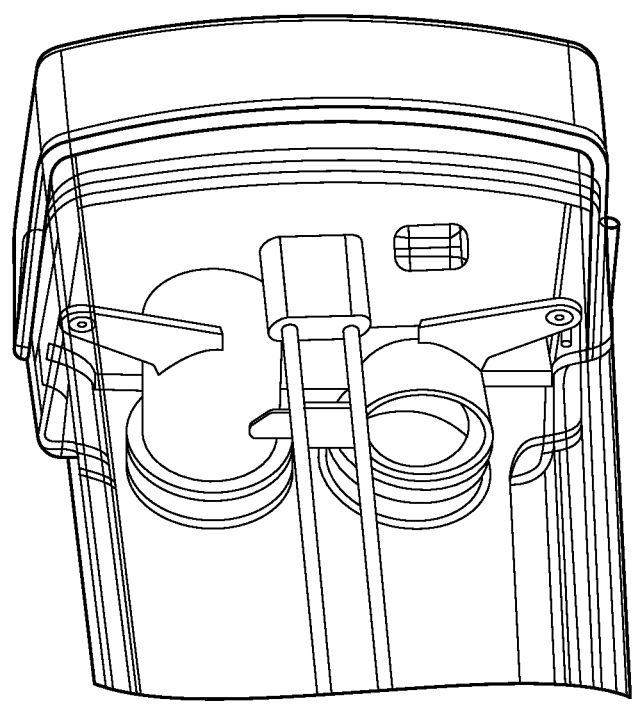
FIG. 19 is a perspective view of a replaceable test chamber cartridge and receiving "closet" of the system shown in FIG. 18, showing a down-bend of an inlet vent, and an up-bend of an exhaust vent of the cartridge.
Figure 20:
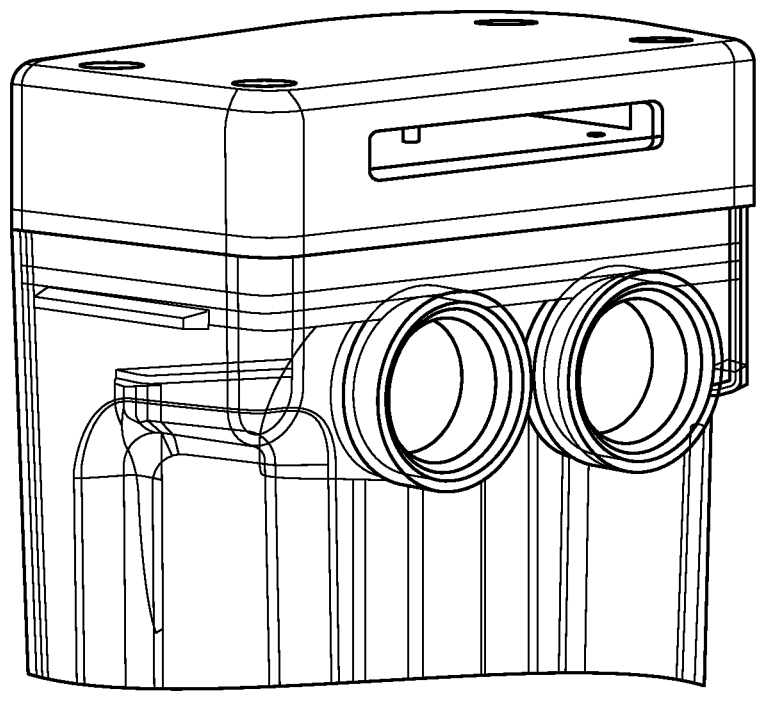
FIG. 20 is a perspective view the cartridge and receiving closet shown in FIG. 19, showing air vent ports and a PC board connector access port of the cartridge.
Figure 21:
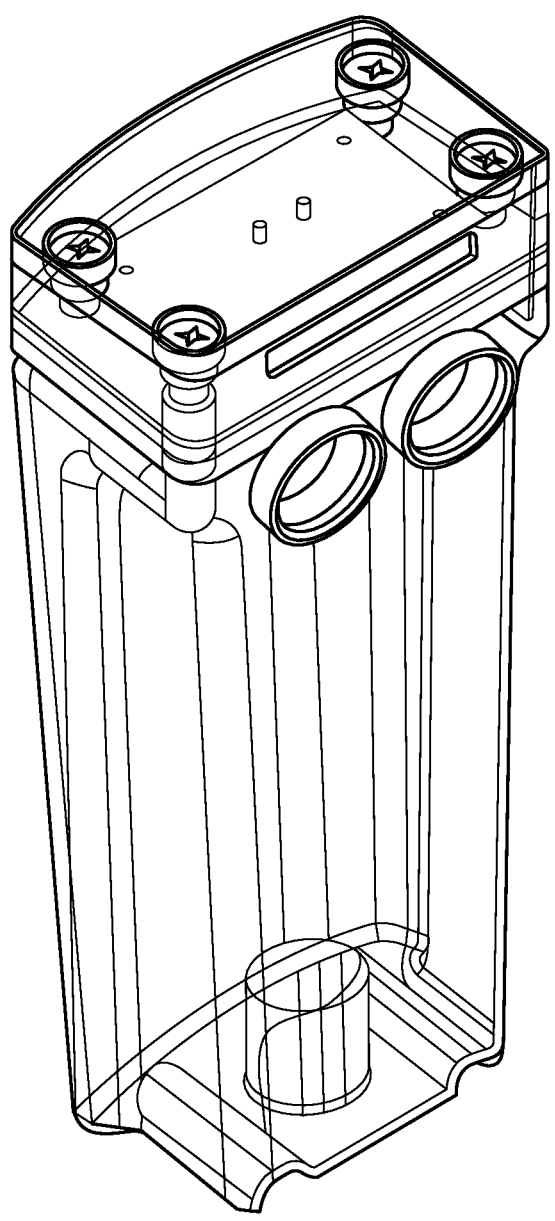
FIG. 21 is a perspective view the cartridge and receiving closet shown in FIGS. 19 and 20, showing a cap PCB, and probe maintenance space of the cartridge and the receiving closet.
Figure 22:
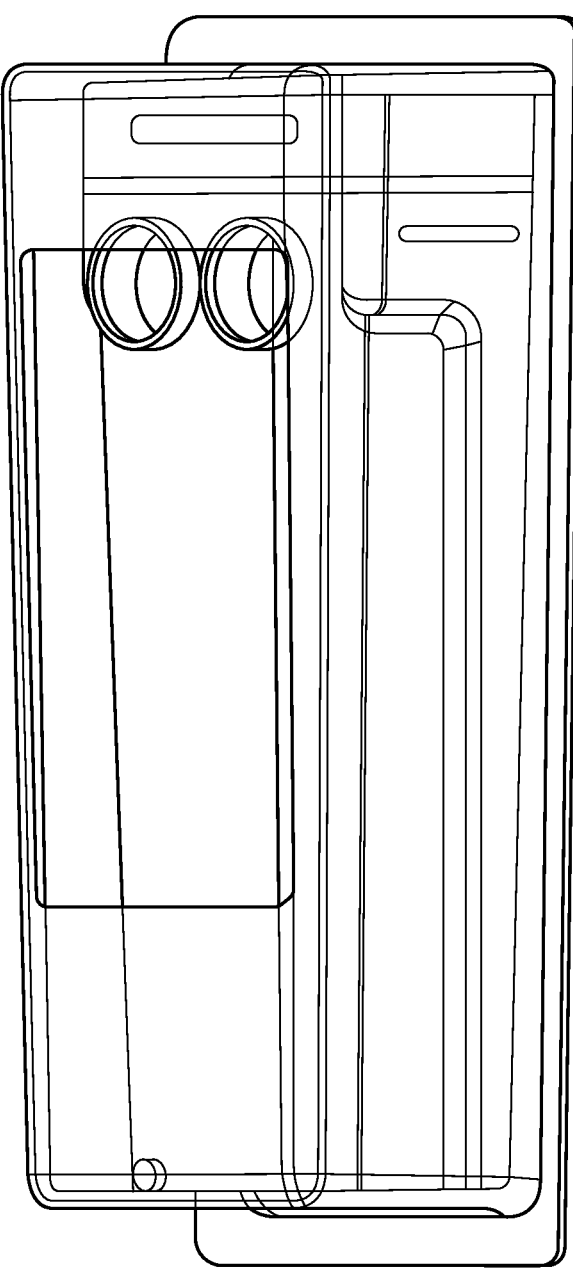
FIG. 22 is a perspective view the cartridge and receiving closet shown in FIGS. 19-21, showing a fit of the cartridge in the receiving closet.

FIG. 17 depicts another alternative embodiment of the system 10 in the form of a system 500.

The system 500 is intended for use where people may be as close as an elbow-length away from each other and may pause or linger in those relative positions for a moment. For example, the system 500 can be used in a teller's cage; a ticket window; a commercial building security point; an information booth; a check-in/check-out station etc.

The system 500 has a top cover that is slitted to encourage mostly sidewise, with some vertical, ingress of air, as driven by a small axial fan within the system 500. The fan speed is chosen to directly ventilate the removable cartridge test chamber within the system 500, at a speed that will not agitate the surface of the reference fluid in the chamber. An angled HEPA filter at the rear balances the incoming air pressure by providing the air an exhaust.

A small alphameric display, approximately one inch tall by three inches wide, is positioned above the cartridge, and its display is configurable in the "Settings" section of the app. Under most circumstances, the display only will display neutral messages such as "Monitoring" and the time/day/date, with the reporting alerts delivered to a facility manager's app.

The system 500 also includes a ring of eight ST Microsystems VLS3LSCX lidar 8 by 8 array sensors bring the system 500 from dormant to alert. The detection range can be reduced to as little as about three to about four feet. A positive detection triggers blinking of the 940 nm IR emitters.

FIGS. 18-21 depict the replaceable test chamber cartridge and receiving "closet."

We claim:

1. A system for detecting a presence of a viral load in an airspace, the system comprising:
   a conductivity probe;
   a frequency generator communicatively coupled to the conductivity probe and configured to, during operation, apply an alternating voltage to the conductivity probe while the conductivity probe is immersed at least in part in a medium comprising a solvent, and particles sampled from the airspace and suspended in the solvent, wherein the frequency generator is configured to apply a first alternating voltage that causes an alternating current to flow between the conductivity probe and the frequency generator; and
   a computing device communicatively coupled to the frequency generator and configured to, during operation, determine a viral load in the medium based on a frequency response of the conductivity probe to the alternating voltage applied to the conductivity probe.

2. The system of claim 1, wherein the computing device is further configured to, during operation, determine the viral load in the medium based on a correlation between the frequency response of the conductivity probe to the alternating voltage applied thereto, and the viral load.

3. The system of claim 1, further comprising the medium, wherein the solvent is one of a liquid or a semi-solid.

4. The system of claim 1, wherein the solvent is selected from a class of materials capable of acting as a base of a colloidal suspension in which the particles are suspended after being separated from the airspace, and further capable of effecting a transfer of charge between the particles and the solvent.

5. The system of claim 1, wherein the solvent is one of deionized water; distilled water; isopropyl alcohol; ultra-low molal tris-salt medium; a mild basic salt medium; and disodium laureth sulfosuccinate medium.

6. The system of claim 1, wherein the solvent has conductivity of one microsiemens or less.

7. The system of claim 1, wherein the computing device is further configured to, during operation, extract one or more signal artifacts from a signal representing the frequency response of the conductivity probe to the alternating voltage applied thereto; and to correlate the viral load in the medium with the one or more signal artifacts to thereby reduce or eliminate false positives and false negatives in the viral load determined by the computing device.

8. The system of claim 7, wherein the signal representing the frequency response of the conductivity probe to the alternating voltage applied thereto is a temporal signal.

9. The system of claim 7, wherein the signal representing the frequency response of the conductivity probe to the alternating voltage applied thereto is a frequency-based signal representing the conductivity of the medium.

10. The system of claim 7, wherein, the computing device is further configured to correlate the one or more signal artifacts with the viral load in the medium using a rule engine developed from a machine learning technique.

11. The system of claim 1, wherein the computing device is further configured to reduce or eliminate false positives and false negatives in the viral load determined by the computing device using at least one of a particulate matter level, a carbon dioxide level, and a presence or absence of people in the airspace.

12. The system of claim 1, wherein:
   the conductivity probe is a first conductivity probe, the frequency generator is a first frequency generator, and the medium is a first medium;
   the system further comprises a second conductivity probe; and a second frequency generator communicatively coupled to the second conductivity probe and configured to, during operation, apply a second alternating voltage to the second conductivity probe while the second conductivity probe is immersed at least in part in a second medium comprising the solvent;
   the second alternating voltage causes a second alternating current to flow between the second conductivity probe and the second frequency generator;
   the system further includes a differential frequency detector communicatively coupled to the first and second frequency generators and the computing device and configured to, during operation, determine a frequency differential between the frequencies of the first and second alternating currents; and
   the computing device is further configured to, during operation, determine the viral load in the first medium based on the frequency differential.

13. The system of claim 12, wherein the second medium is free of virus particles.

14. The system of claim 12, wherein: the computing device is further configured to determine a pattern difference between signals representing the frequency responses of the first and second conductivity probes to the respective first and second alternating voltages applied thereto; and the patterns are artifacts of the signals representing the frequency responses of the first and second conductivity probes.

15. The system of claim 12, wherein the computing device is further configured to, during operation, determine the viral load in the first medium using one of a homodyne and a heterodyne detection technique.

16. The system of claim 12, wherein the computing device is further configured to estimate the viral load in the airspace based on the viral load in the first medium.

17. The system of claim 1, wherein, the computing device is further configured to generate and send a notification when the viral load in the airspace is determined to be greater than a predetermined value.

18. The system of claim 1, wherein:

the system further comprises a visual altering device communicatively coupled to the computing device;

the computing device is further configured to generate an output when the viral load in the airspace is determined to be greater than a predetermined value; and the visual alerting device is configured to generate a visual alert in response to the output of the computing device.

19. The system of claim 1, wherein:

the system further comprises an audible altering device communicatively coupled to the computing device;

the computing device is further configured to generate an output when the viral load in the airspace is determined to be greater than a predetermined value; and the audible alerting device is configured to generate an audible alert in response to the output of the computing device.

20. The system of claim 1, wherein computing device is an edge-cloud server.

21. The system of claim 1, wherein the system further comprises a particle collector in fluid communication with the airspace and configured to, during operation, separate the particles from a sample of the airspace.

22. The system of claim 21, wherein, the particle collector comprises a coarse filter configured to remove from the sample of the airspace particles having a size greater than a predetermined value.

23. The system of claim 22, wherein the coarse filter is configured to remove from the sample of the airspace particles having an aerodynamic diameter greater than ten microns.

24. The system of claim 22, wherein the particle collector further comprises a particle separator configured to remove from the sample of the airspace the particles sampled from the airspace.

25. The system of claim 1, further comprising a tube in fluid communication with an interior of a chamber holding the solvent, wherein the tube is configured so that an individual can breathe into the tube and thereby introduce the virus into the solvent via the tube.

* * * * *